US008070718B2

(12) United States Patent
Weber et al.

(10) Patent No.: US 8,070,718 B2
(45) Date of Patent: Dec. 6, 2011

(54) MEDICAL DEVICES FORMED WITH A SACRIFICIAL STRUCTURE AND PROCESSES OF FORMING THE SAME

(75) Inventors: Jan Weber, Maple Grove, MN (US); Scott Schewe, Eden Prairie, MN (US); Thomas J. Holman, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2122 days.

(21) Appl. No.: 11/010,810

(22) Filed: Dec. 13, 2004

(65) Prior Publication Data

US 2006/0129179 A1    Jun. 15, 2006

(51) Int. Cl.
*A61M 29/00* (2006.01)
*B29C 33/40* (2006.01)

(52) U.S. Cl. ............. 604/96.01; 604/500; 128/898; 264/219; 264/221; 264/225

(58) Field of Classification Search ........... 604/101.09, 604/101.02, 96.01, 500; 264/221, 224–227, 264/169, 135, 219, 220; 156/86; 128/898
See application file for complete search history.

(56) References Cited

U.S. PATENT DOCUMENTS

| | | | |
|---|---|---|---|
| 2,481,488 A | 9/1949 | Auzin | 156/242 |
| 2,690,595 A | 10/1954 | Raiche | 18/58.7 |
| 3,304,353 A | 2/1967 | Harautuneian | 264/515 |
| 3,879,516 A * | 4/1975 | Wolvek | 264/135 |
| 4,490,421 A | 12/1984 | Levy | 428/35 |
| 4,497,074 A | 2/1985 | Rey et al. | 623/1.24 |
| 4,892,544 A * | 1/1990 | Frisch | 128/898 |
| 5,112,900 A | 5/1992 | Buddenhagen et al. | 524/484 |
| 5,195,969 A | 3/1993 | Wang et al. | 604/96 |
| 5,223,205 A | 6/1993 | Jackowski et al. | 264/521 |
| 5,254,089 A | 10/1993 | Wang | 604/96 |
| 5,304,197 A | 4/1994 | Pinchuk et al. | 606/194 |
| 5,348,538 A | 9/1994 | Wang et al. | 604/96 |
| 5,389,314 A | 2/1995 | Wang | 264/25 |
| 5,403,340 A | 4/1995 | Wang et al. | 606/194 |
| 5,409,458 A | 4/1995 | Khairkhahan et al. | 604/103.08 |
| 5,425,723 A | 6/1995 | Wang | 604/280 |
| 5,439,443 A | 8/1995 | Miyata et al. | 604/96 |
| 5,447,497 A | 9/1995 | Sogard et al. | 604/101 |
| 5,449,371 A | 9/1995 | Pinchuk et al. | 606/194 |
| 5,458,575 A | 10/1995 | Wang | 604/101 |
| 5,499,980 A | 3/1996 | Euteneuer | 606/28 |
| 5,512,051 A | 4/1996 | Wang | 604/96 |
| 5,549,552 A | 8/1996 | Peters et al. | 604/96 |

(Continued)

FOREIGN PATENT DOCUMENTS

EP    0934755    8/1999

(Continued)

OTHER PUBLICATIONS

U.S. Appl. No. 10/622,621, filed Jul. 18, 2003, Weber et al.

(Continued)

*Primary Examiner* — Nicholas D Lucchesi
*Assistant Examiner* — Leah Stohr
(74) *Attorney, Agent, or Firm* — Vidas, Arrett & Steinkraus, P.A.

(57) ABSTRACT

Medical devices formed using a sacrificial structure, and processes of forming the devices therefrom.

23 Claims, 49 Drawing Sheets

U.S. PATENT DOCUMENTS

| | | | |
|---|---|---|---|
| 5,549,553 A | 8/1996 | Ressemann et al. | 604/103.08 |
| 5,550,180 A | 8/1996 | Elsik et al. | 524/430 |
| 5,556,383 A | 9/1996 | Wang et al. | 604/96 |
| 5,704,913 A | 1/1998 | Abele et al. | 604/101 |
| 5,738,653 A | 4/1998 | Pinchuk et al. | 604/96 |
| 5,772,864 A * | 6/1998 | Møller et al. | 205/73 |
| 5,826,588 A | 10/1998 | Forman | 128/898 |
| 5,830,182 A | 11/1998 | Wang et al. | 604/96 |
| 5,833,706 A | 11/1998 | Germain et al. | 606/194 |
| 5,951,941 A | 9/1999 | Wang et al. | 264/523 |
| 6,030,371 A * | 2/2000 | Pursley | 604/527 |
| 6,110,142 A | 8/2000 | Pinchuk et al. | 604/96 |
| 6,113,579 A | 9/2000 | Eidenschink et al. | 604/264 |
| 6,136,258 A | 10/2000 | Wang et al. | 264/514 |
| 6,146,356 A | 11/2000 | Wang et al. | 604/96 |
| 6,156,254 A | 12/2000 | Andrews et al. | 261/231 |
| 6,171,278 B1 | 1/2001 | Wang et al. | 604/96 |
| 6,193,738 B1 | 2/2001 | Tomaschko et al. | 606/194 |
| 6,224,803 B1 | 5/2001 | Tiernan | 264/166 |
| 6,242,063 B1 * | 6/2001 | Ferrera et al. | 428/35.2 |
| 6,328,710 B1 | 12/2001 | Wang et al. | 604/96.01 |
| 6,328,925 B1 | 12/2001 | Wang et al. | 264/512 |
| 6,406,457 B1 | 6/2002 | Wang et al. | 604/96.01 |
| 6,482,348 B1 | 11/2002 | Wang et al. | 264/514 |
| 6,500,146 B1 | 12/2002 | Pinchuk et al. | 604/96.01 |
| 6,500,148 B1 | 12/2002 | Pinchuk et al. | 604/103.11 |
| 6,514,228 B1 | 2/2003 | Hamilton et al. | 604/96.01 |
| 6,517,515 B1 | 2/2003 | Eidenschink | 604/101.05 |
| 6,746,425 B1 | 6/2004 | Beckham | 604/103.09 |
| 2002/0007203 A1 * | 1/2002 | Gilmartin et al. | 607/105 |
| 2002/0165600 A1 | 11/2002 | Banas et al. | 623/1.11 |
| 2003/0018387 A1 | 1/2003 | Schuessler | 623/8 |
| 2003/0028212 A1 * | 2/2003 | Saab | 606/192 |
| 2005/0015046 A1 * | 1/2005 | Weber et al. | 604/96.01 |

FOREIGN PATENT DOCUMENTS

WO      0153559      7/2001

OTHER PUBLICATIONS

U.S. Appl. No. 10/862,250, filed Jun. 7, 2004, Mapes et al.

\* cited by examiner

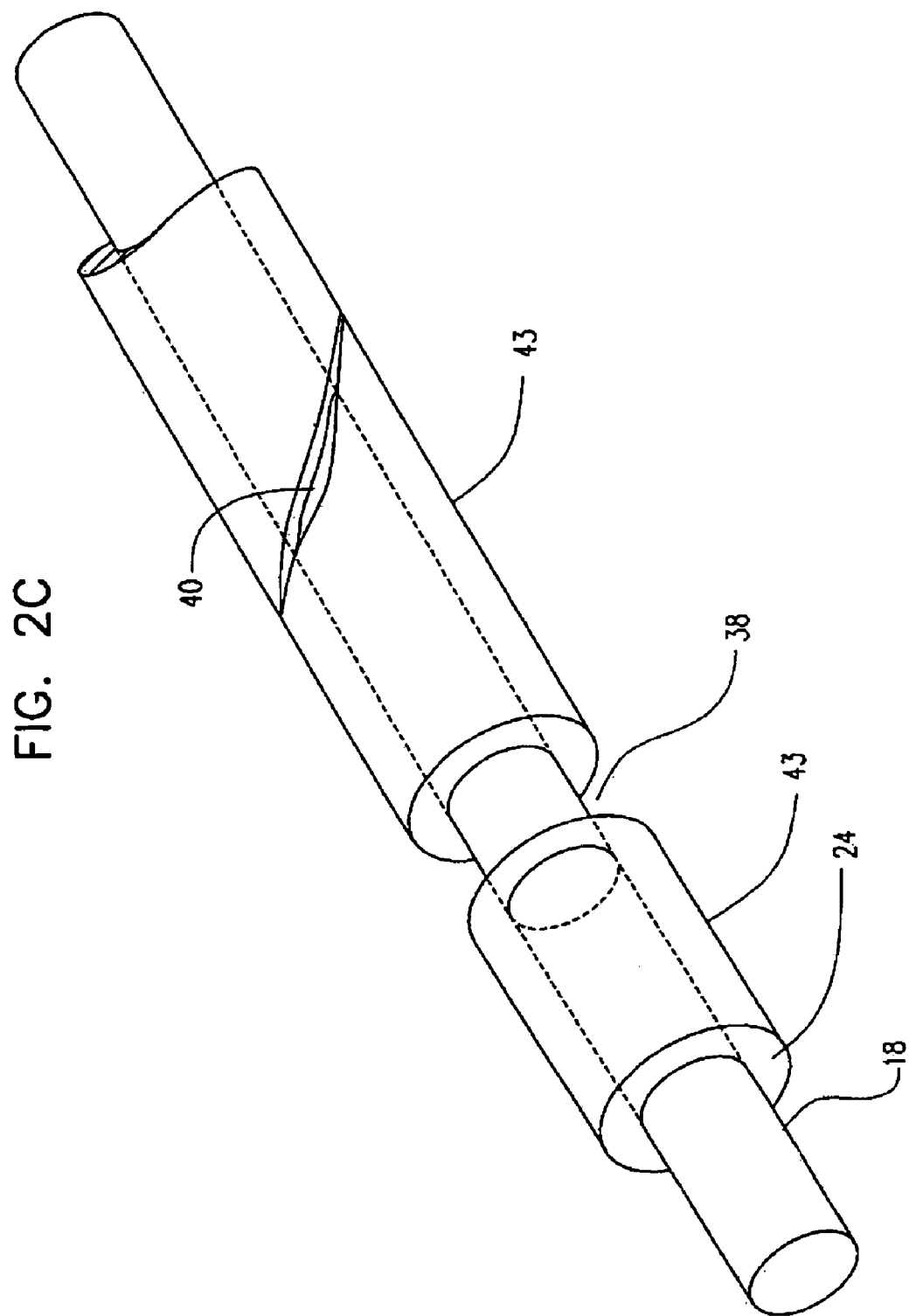

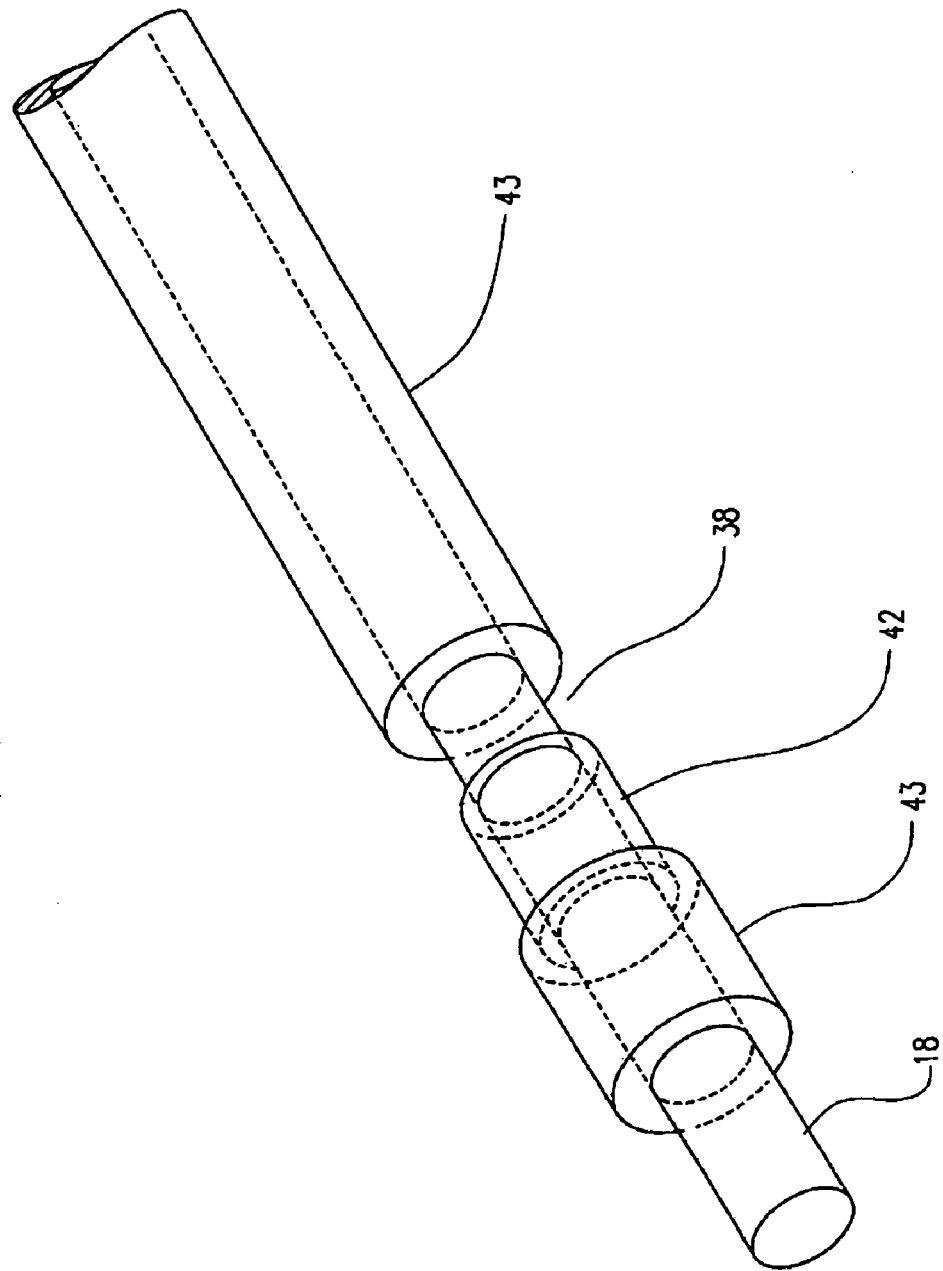

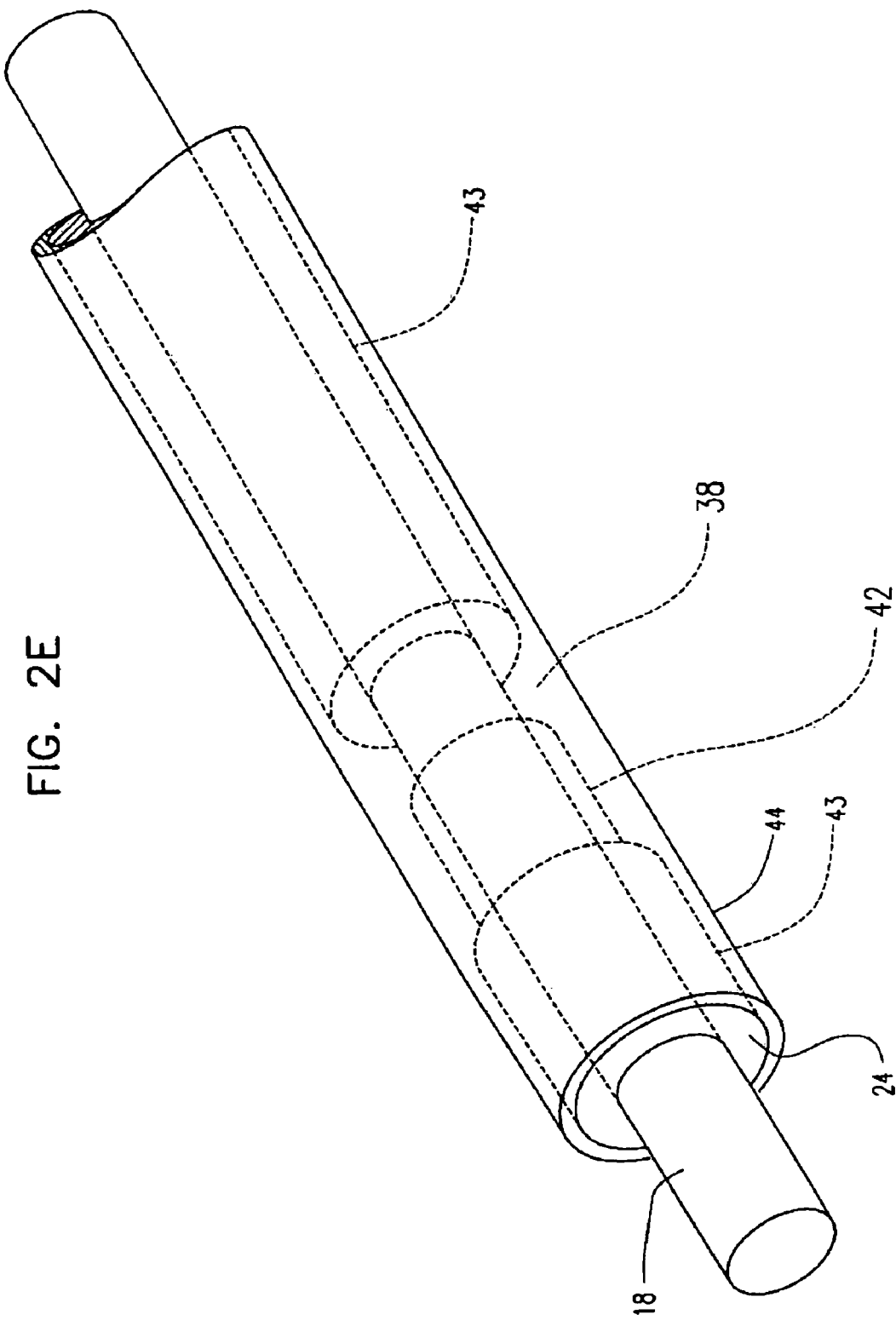

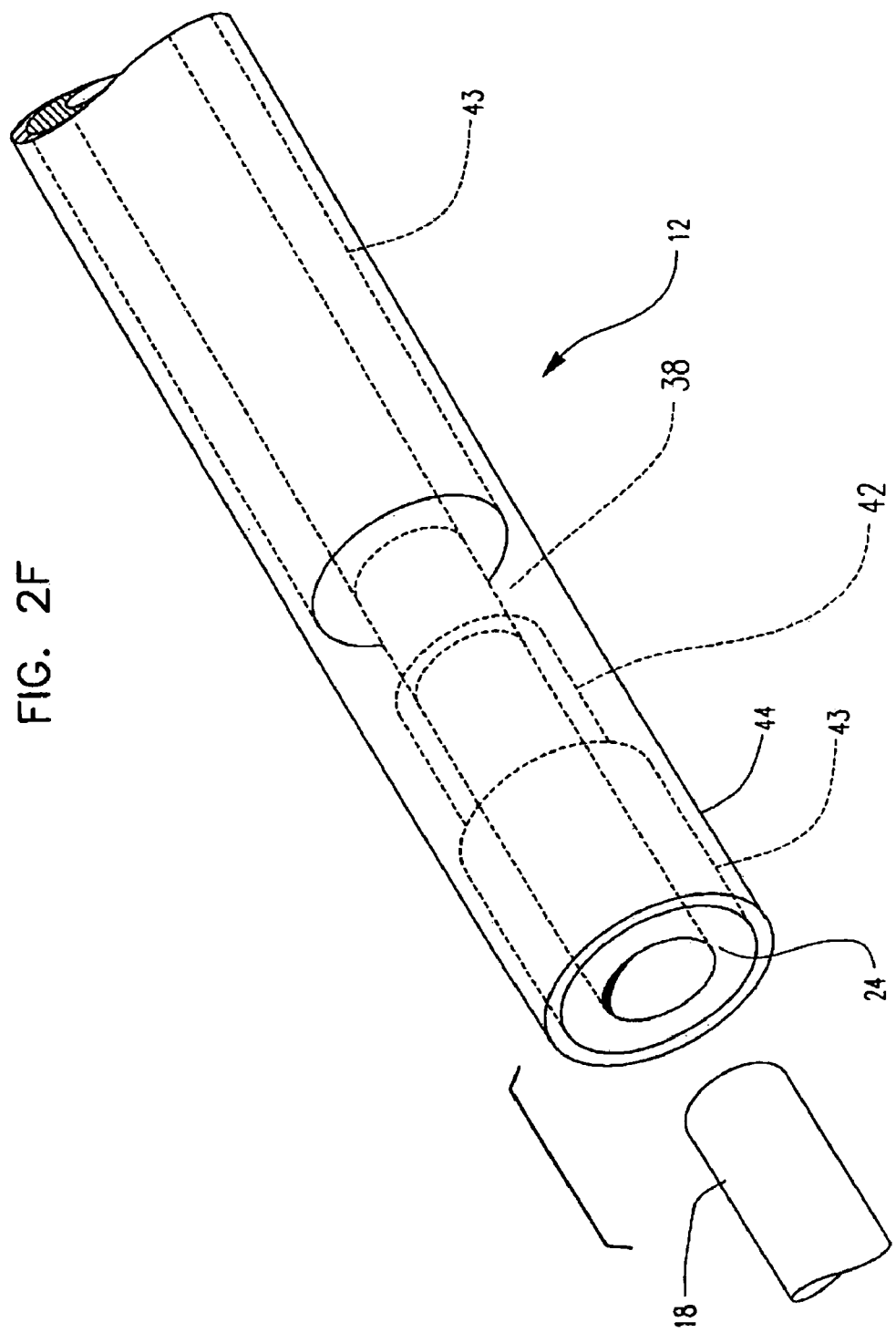

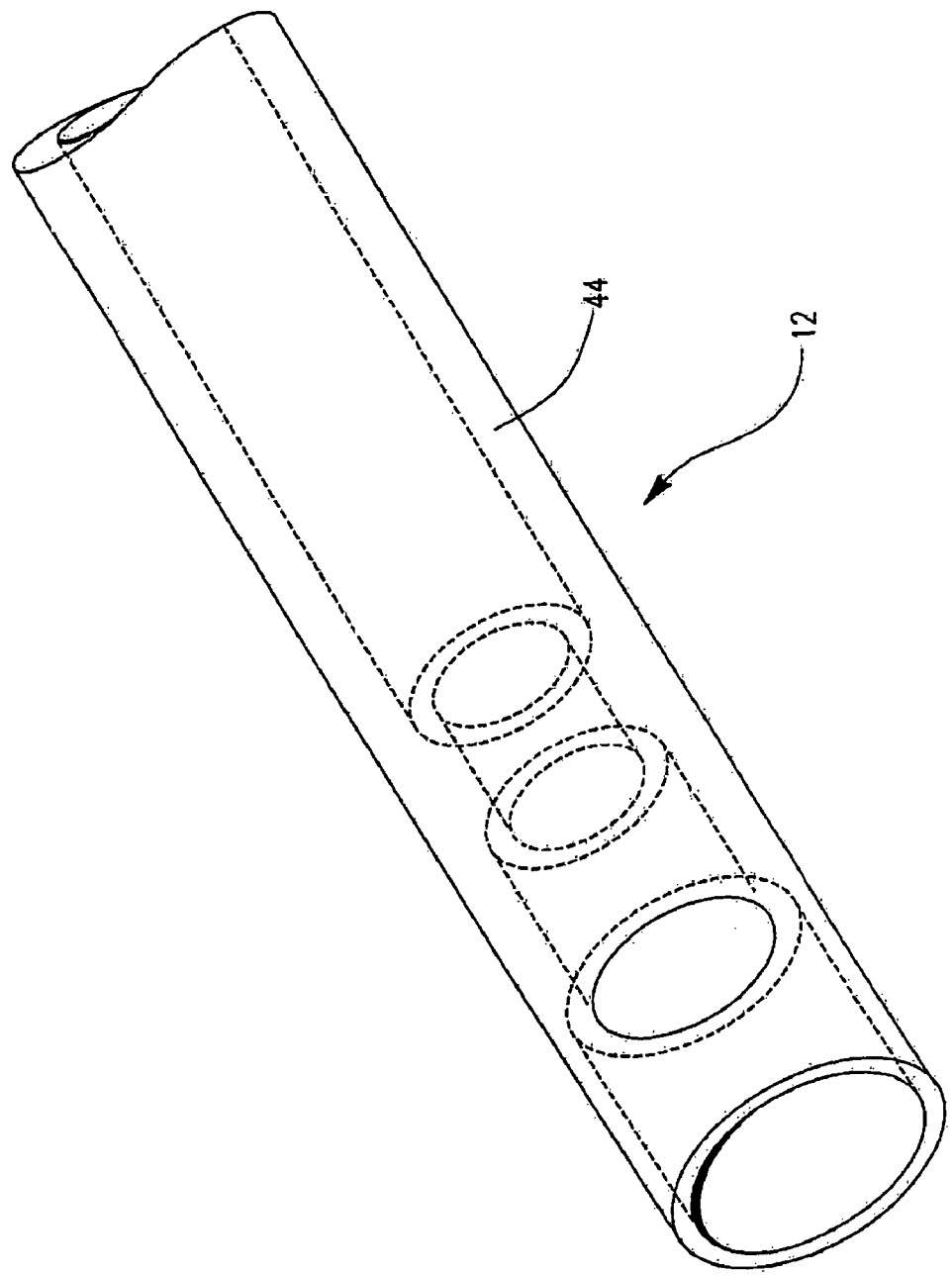

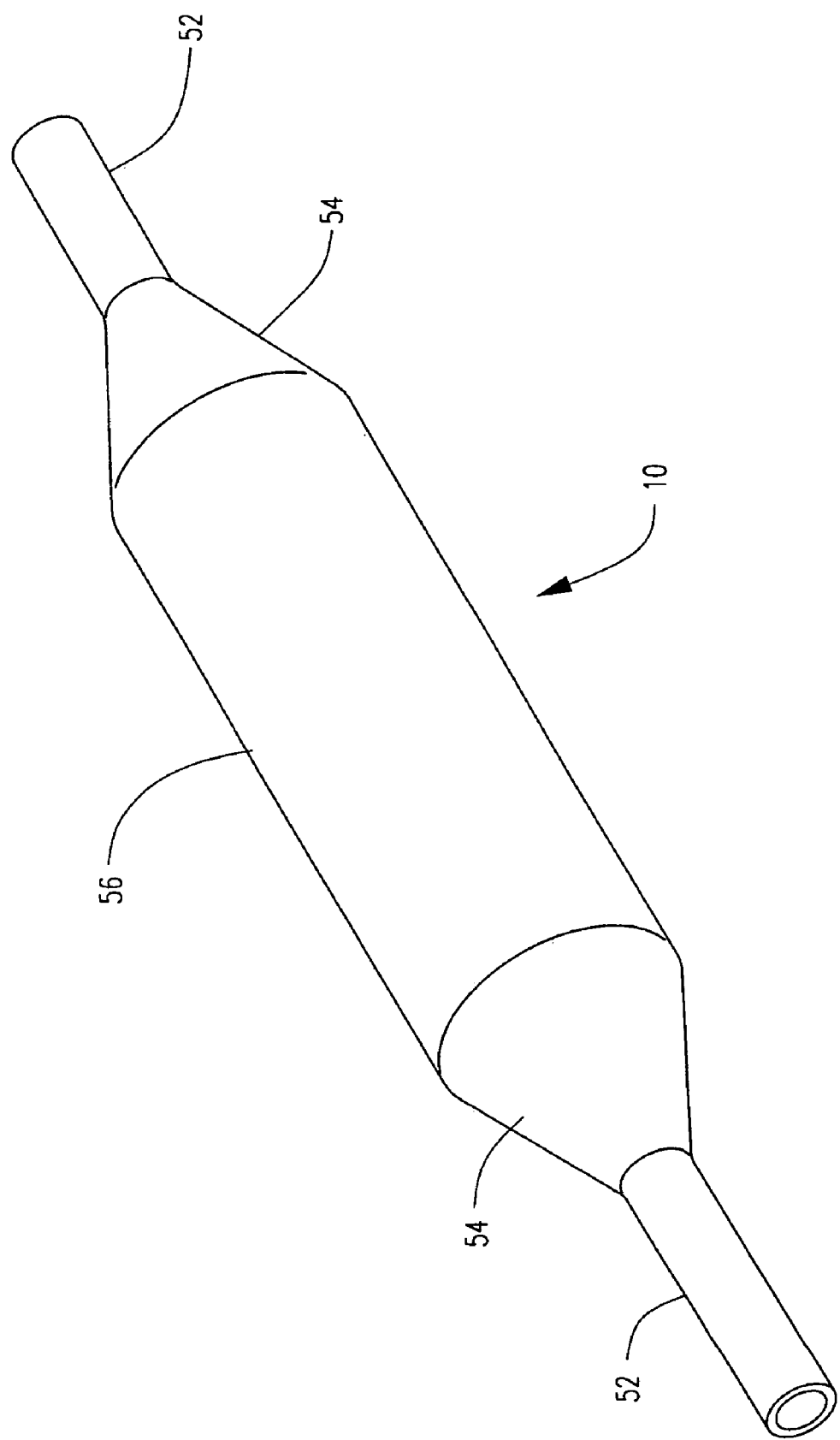

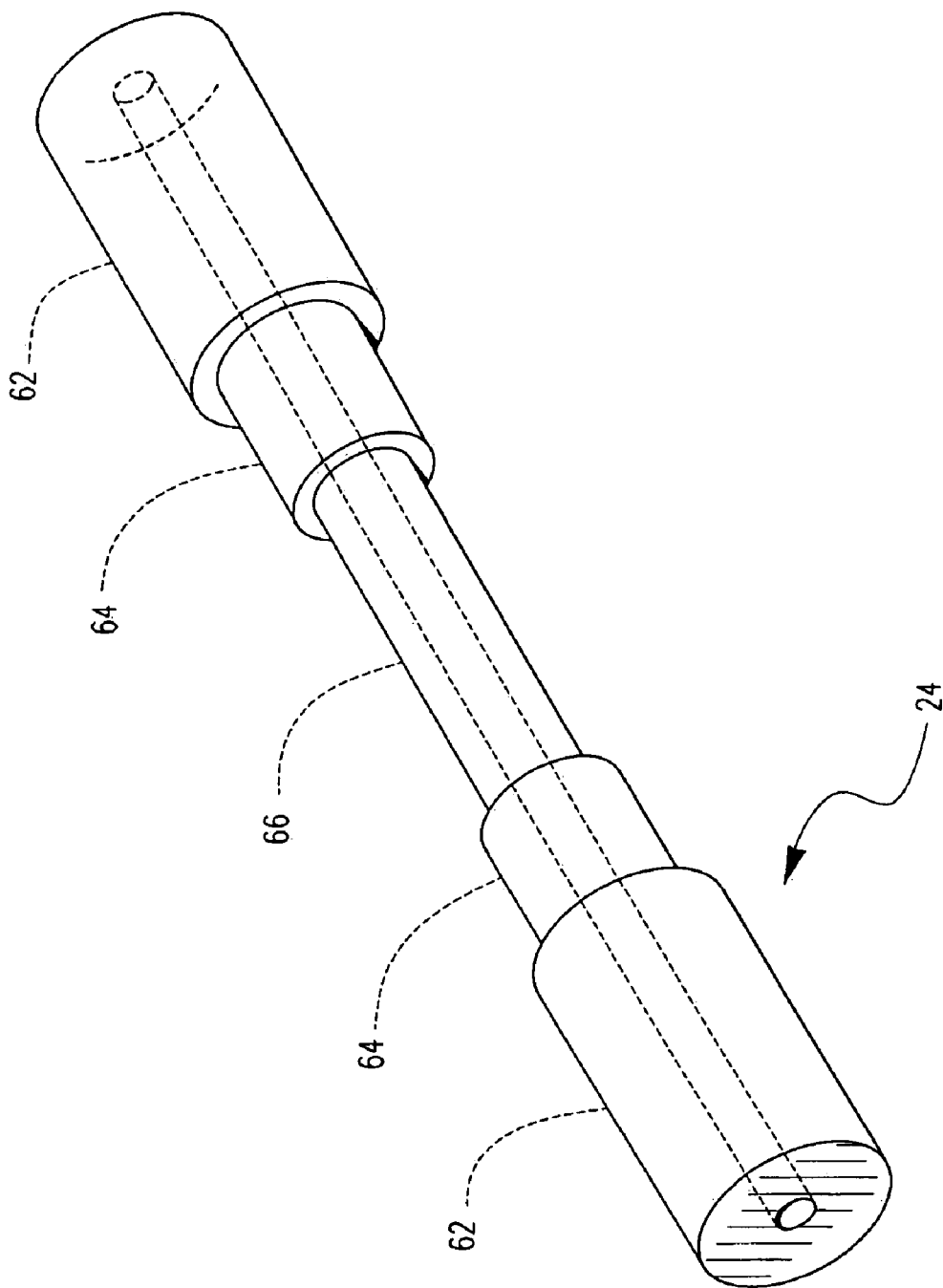

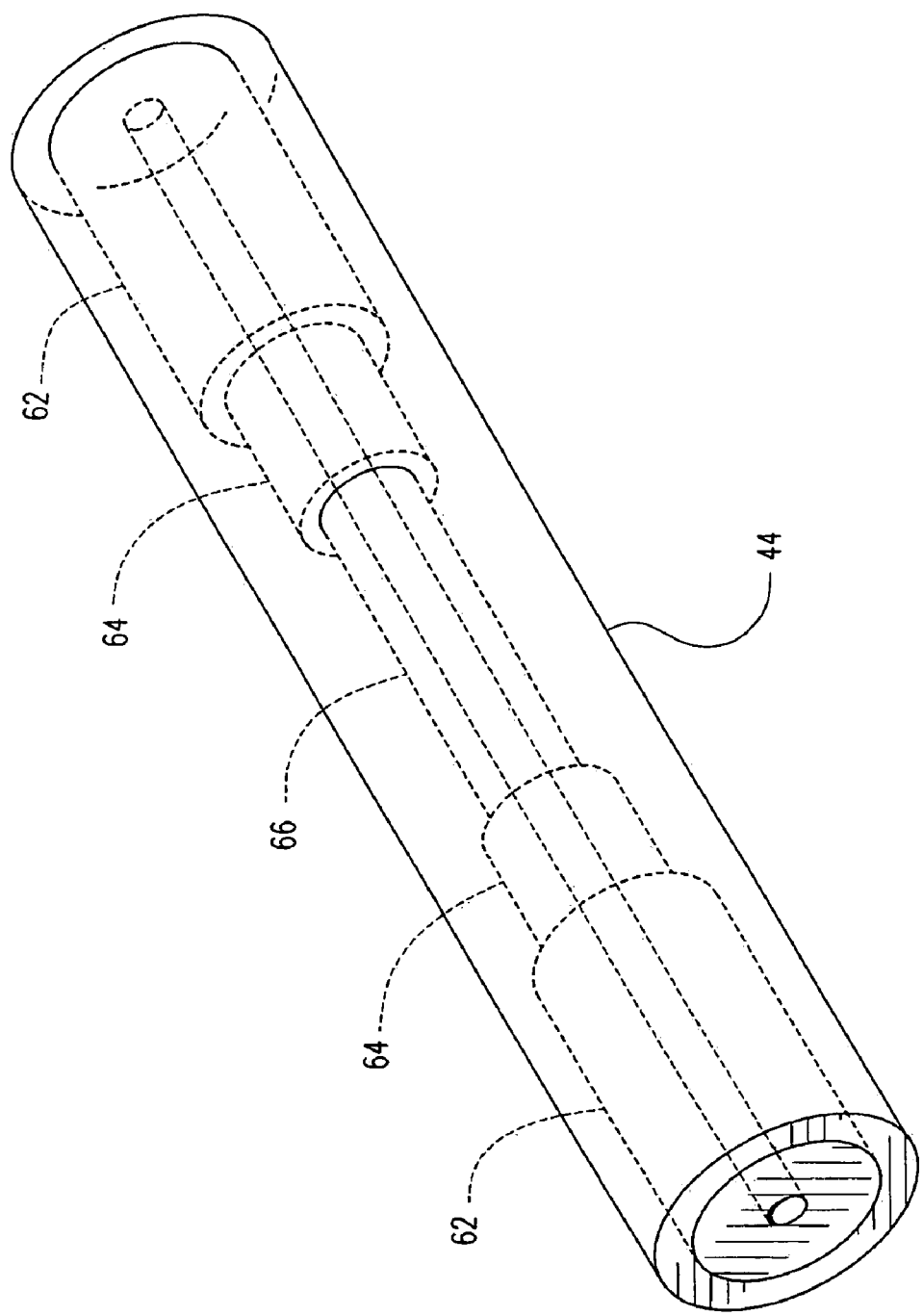

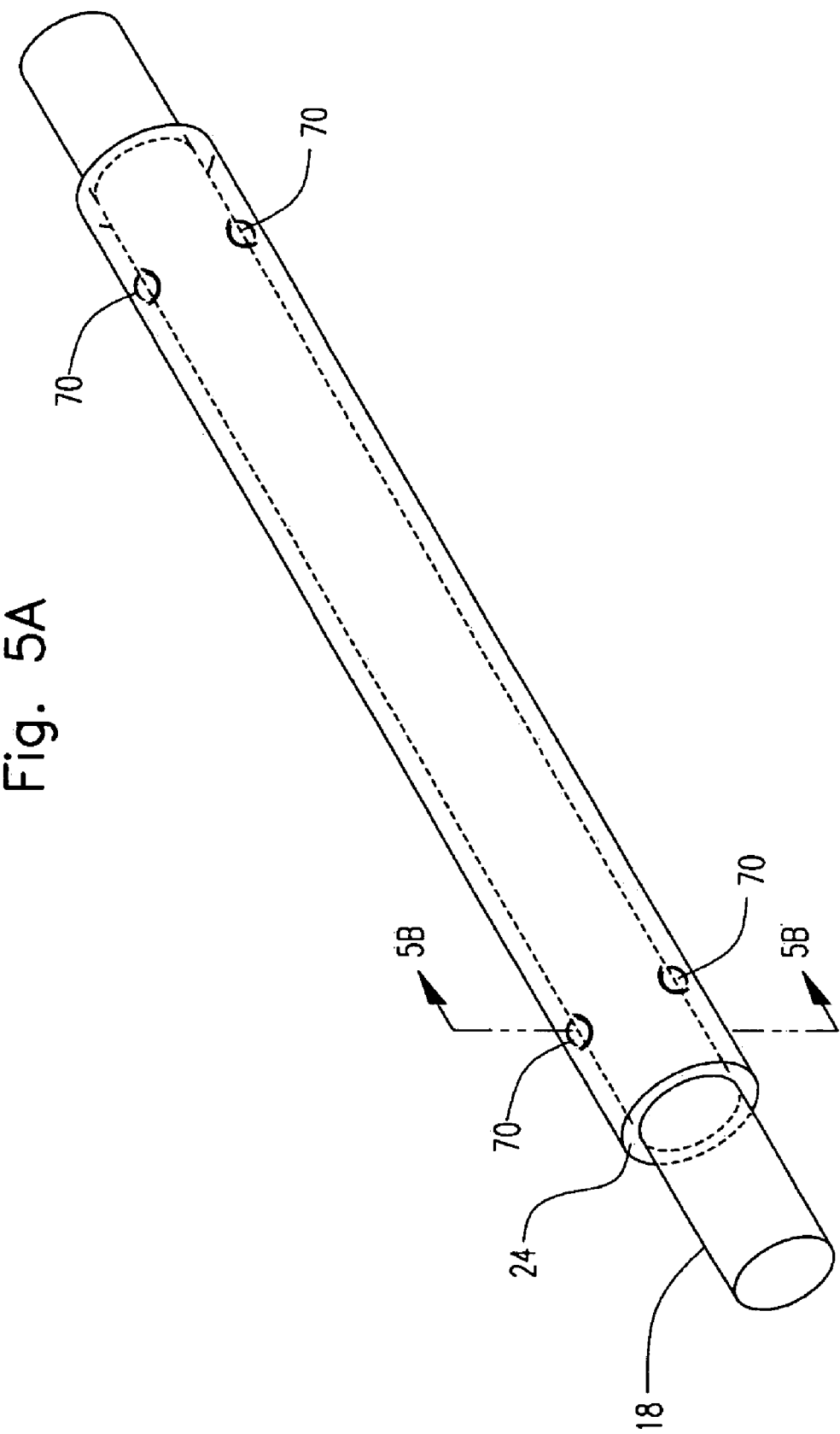

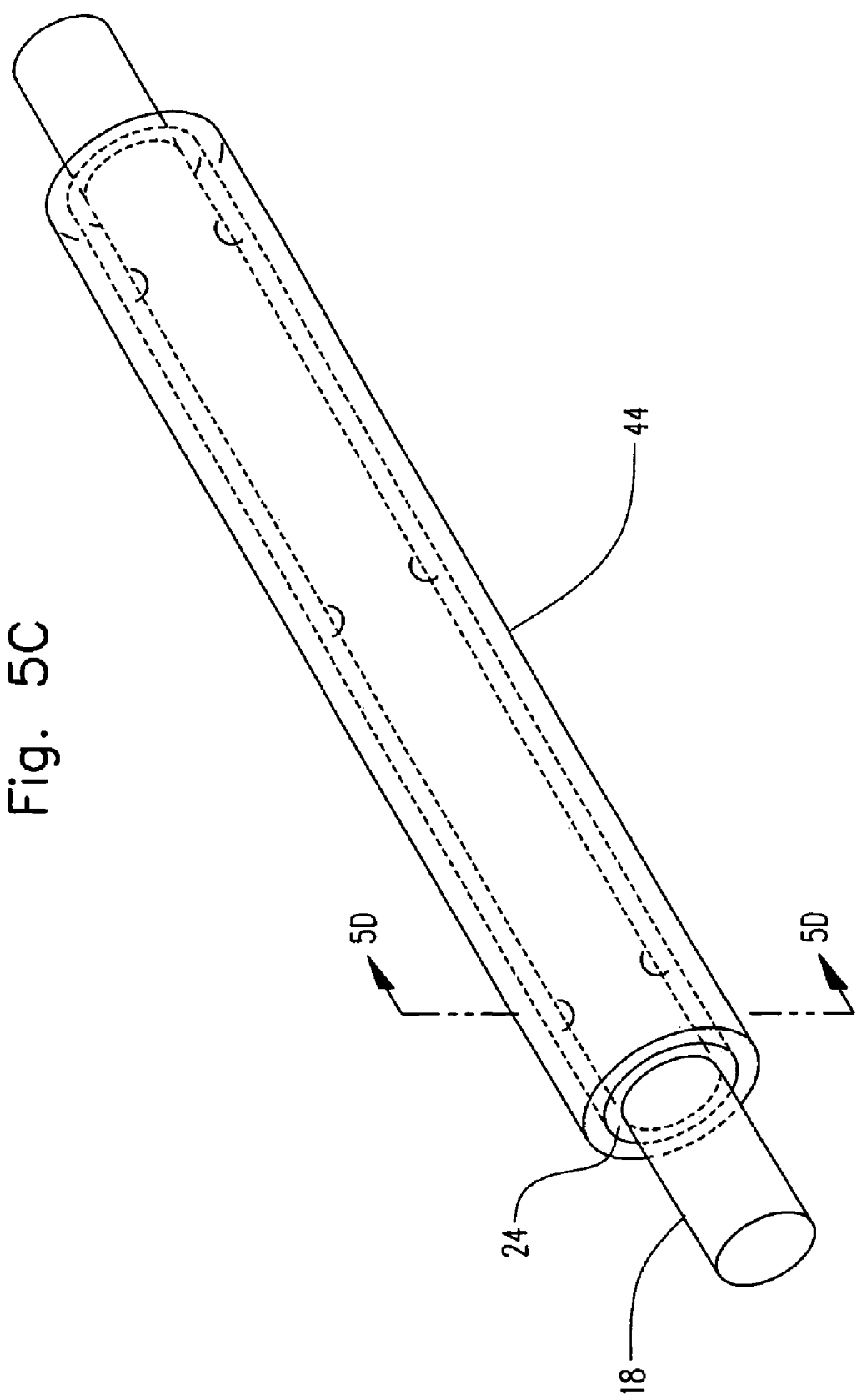

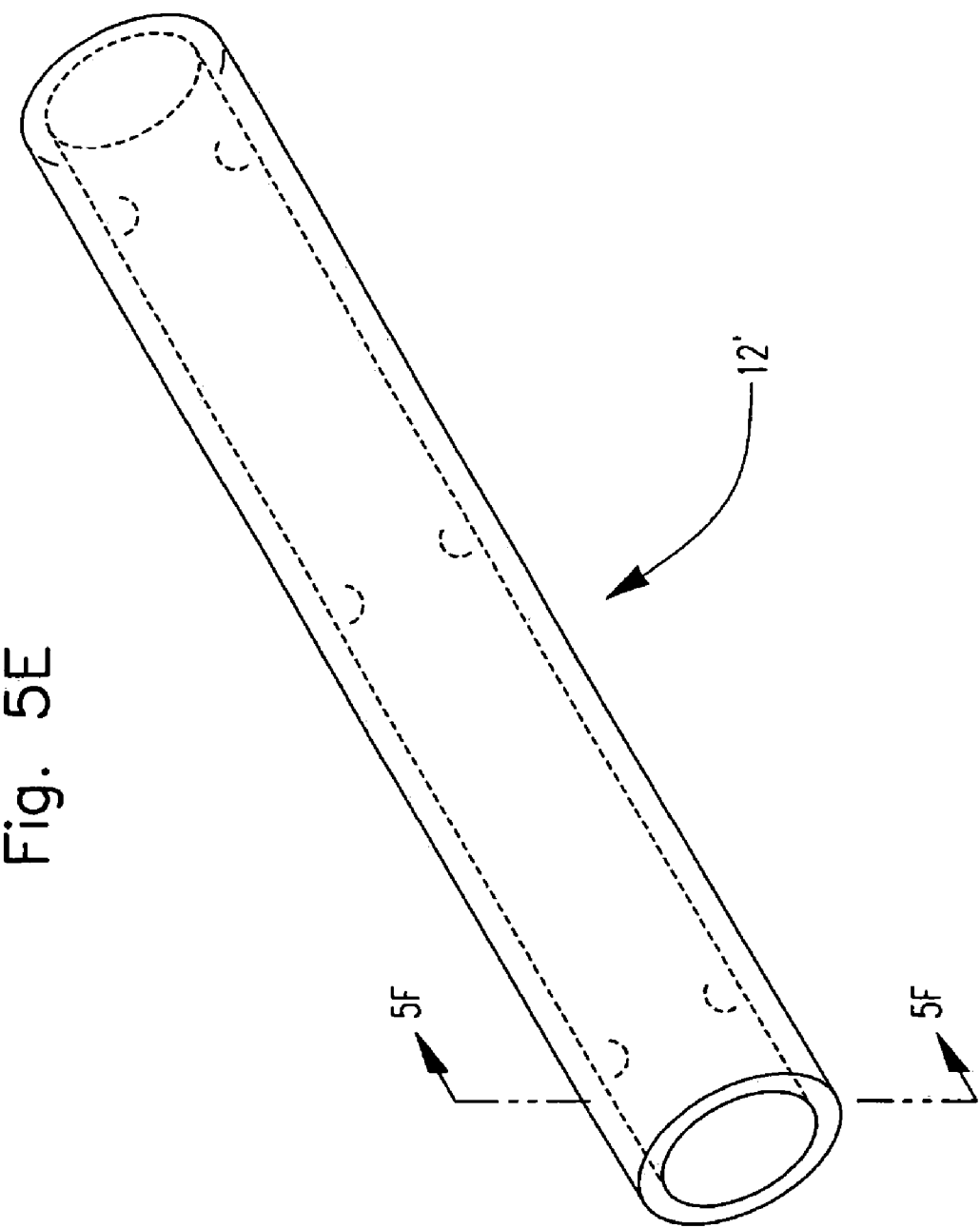

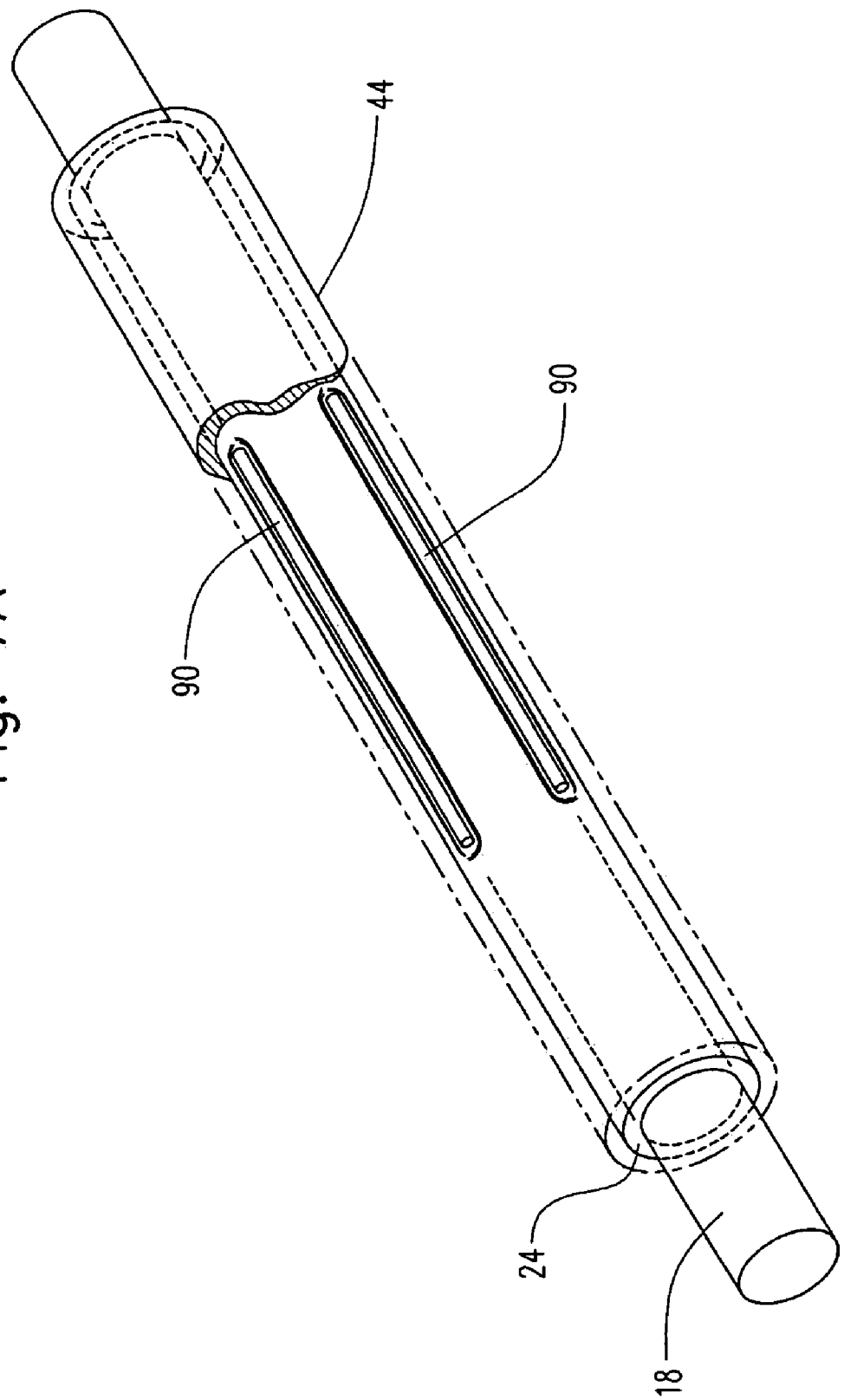

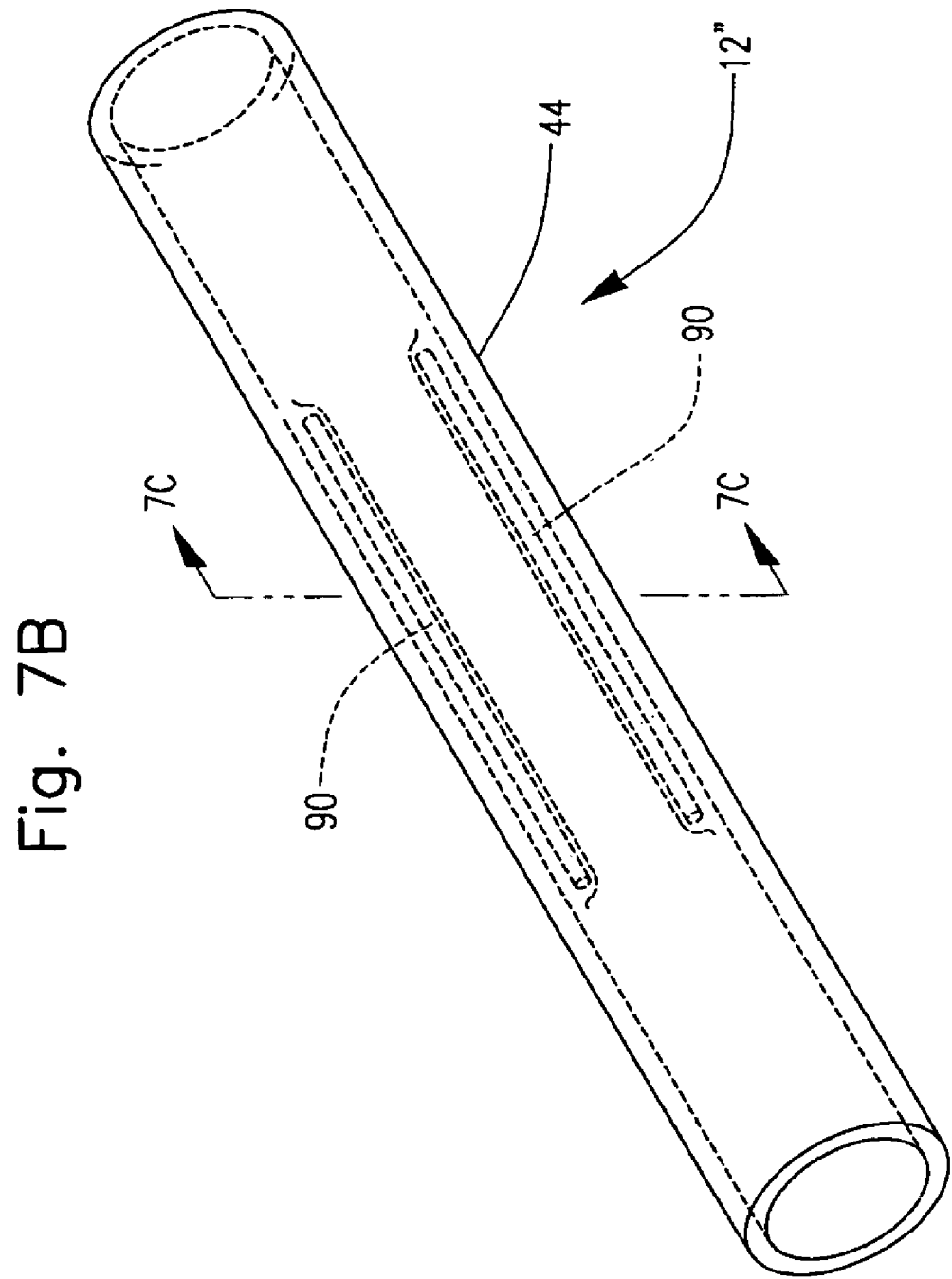

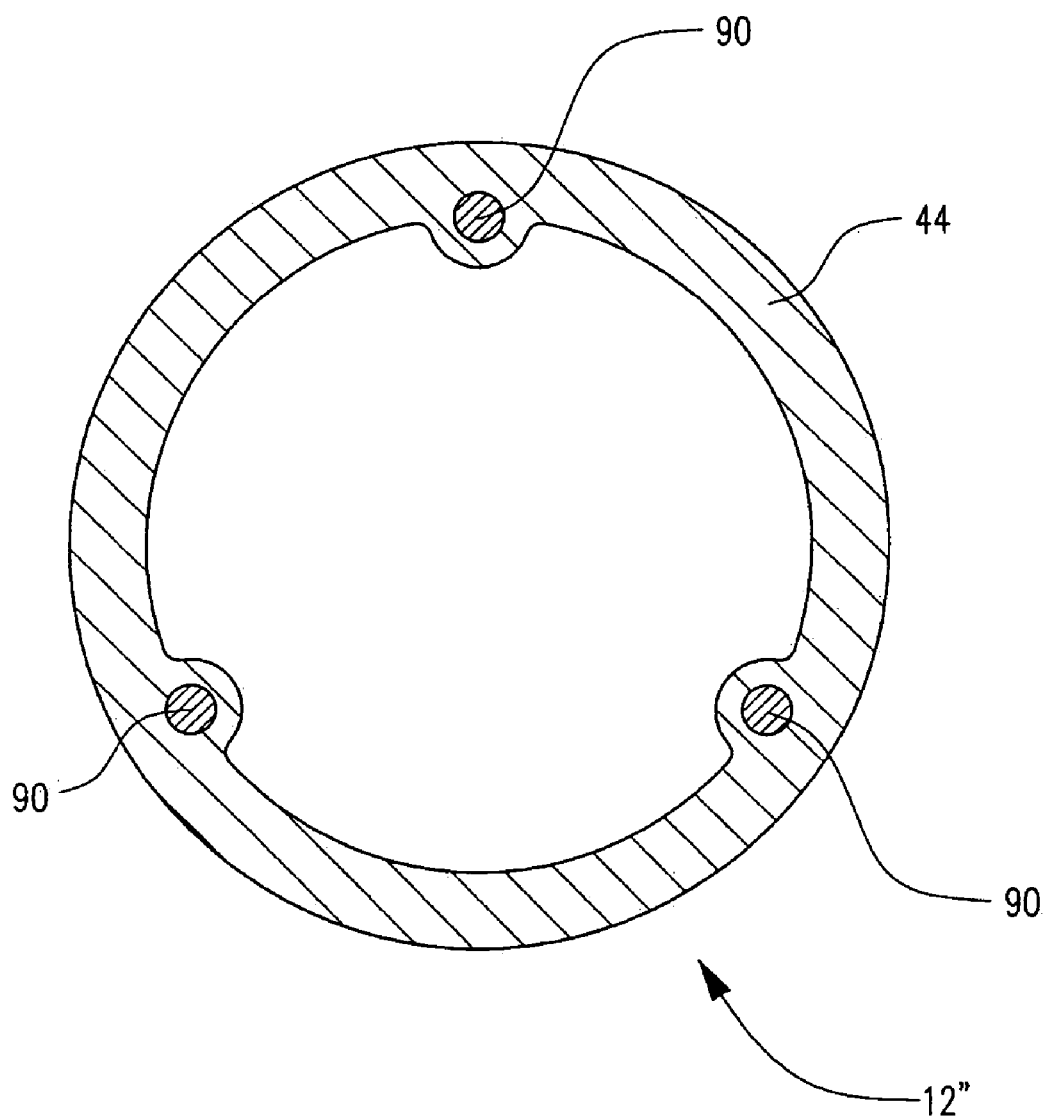

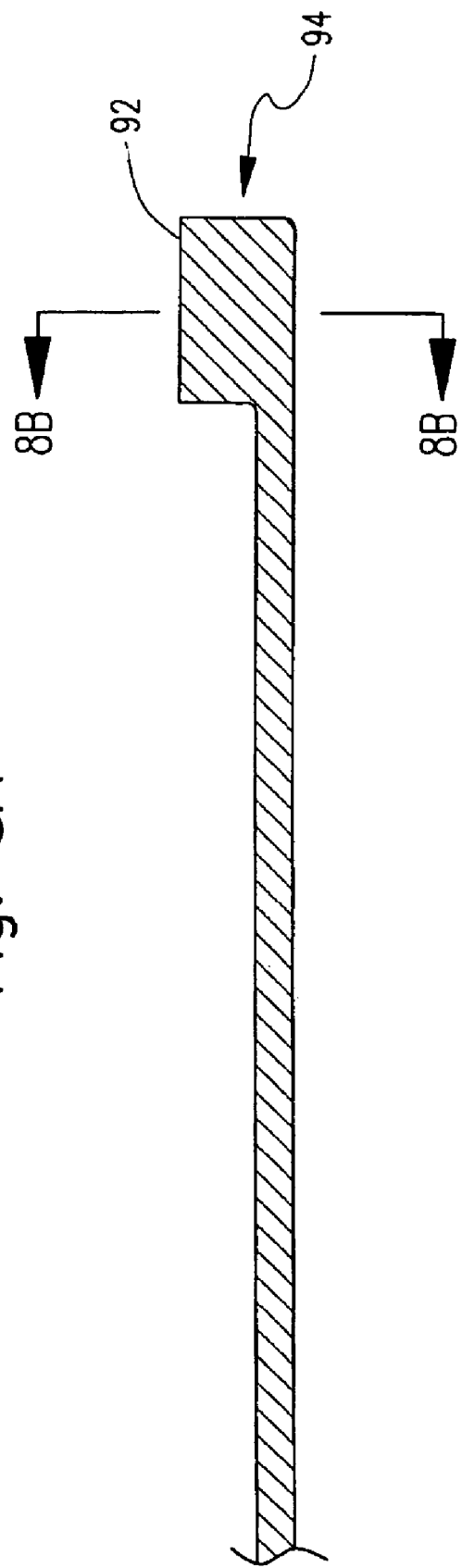

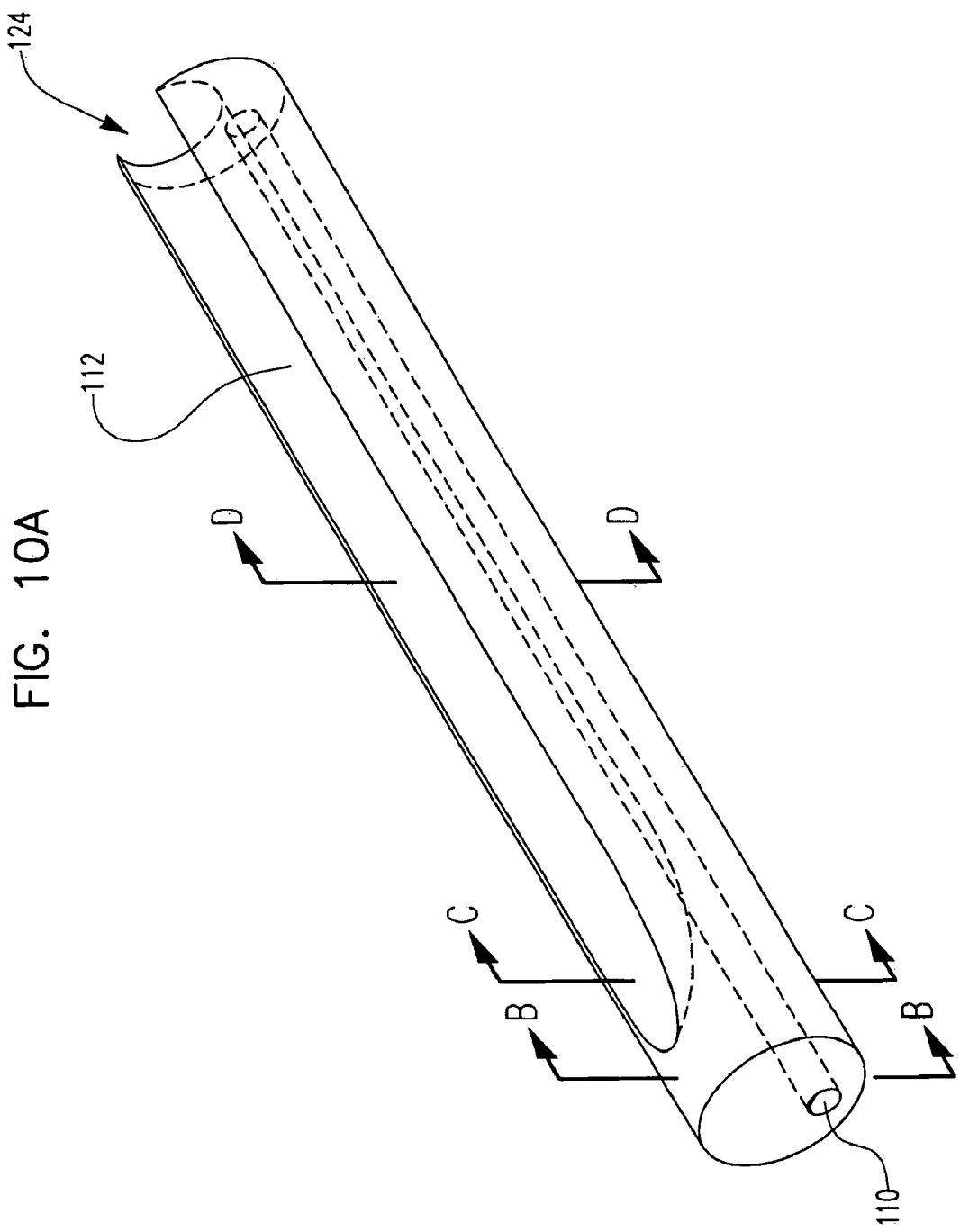

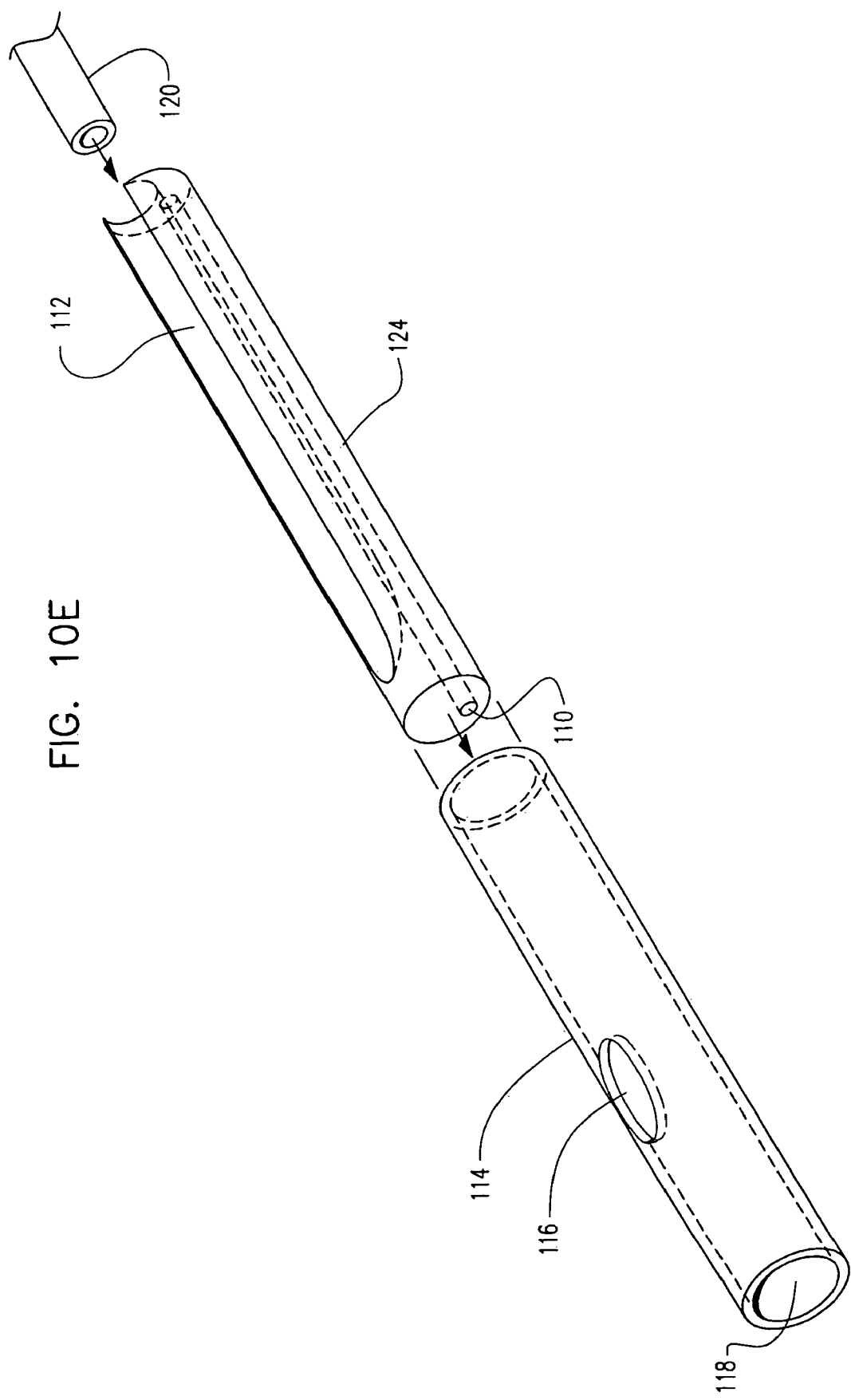

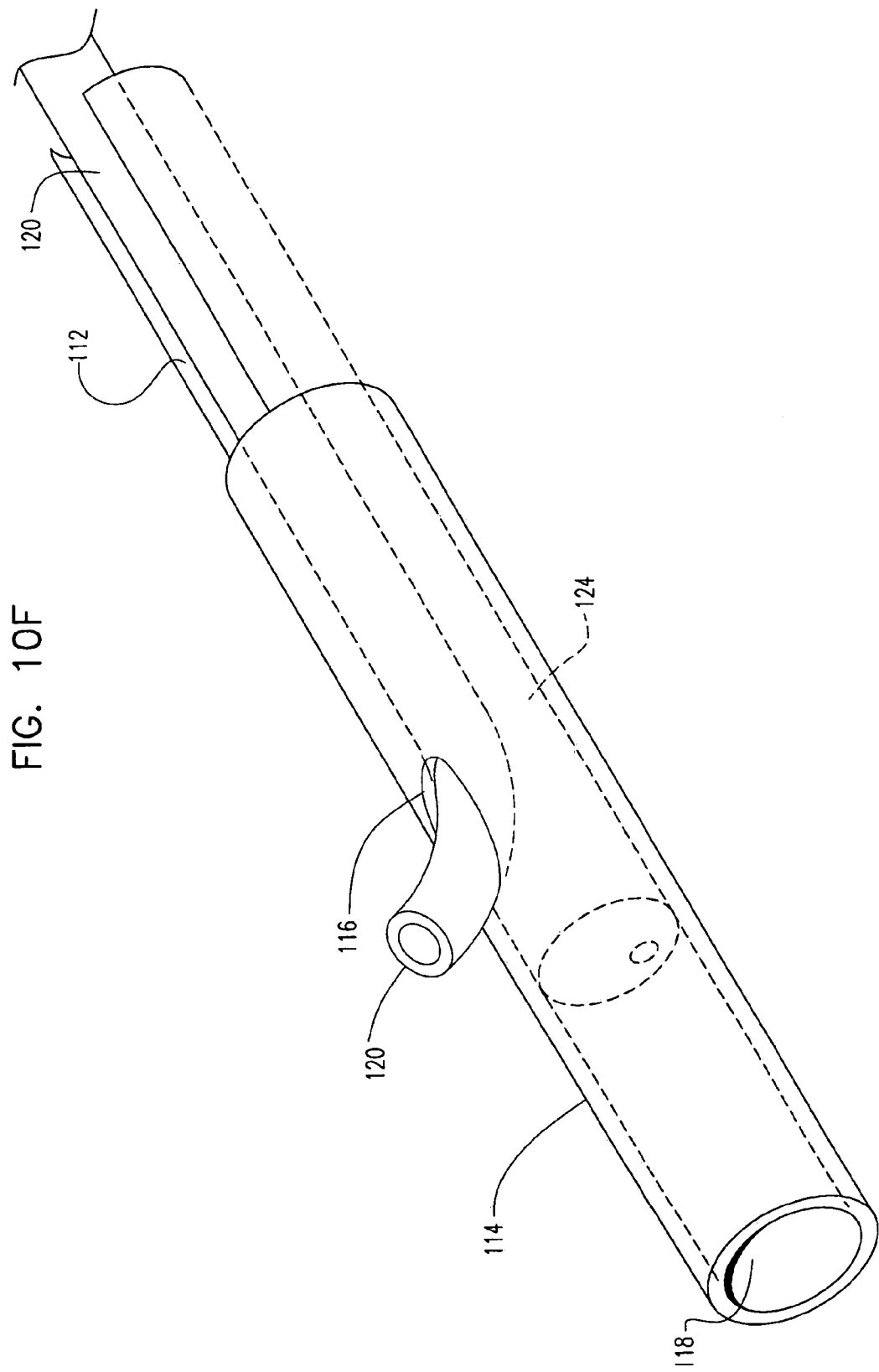

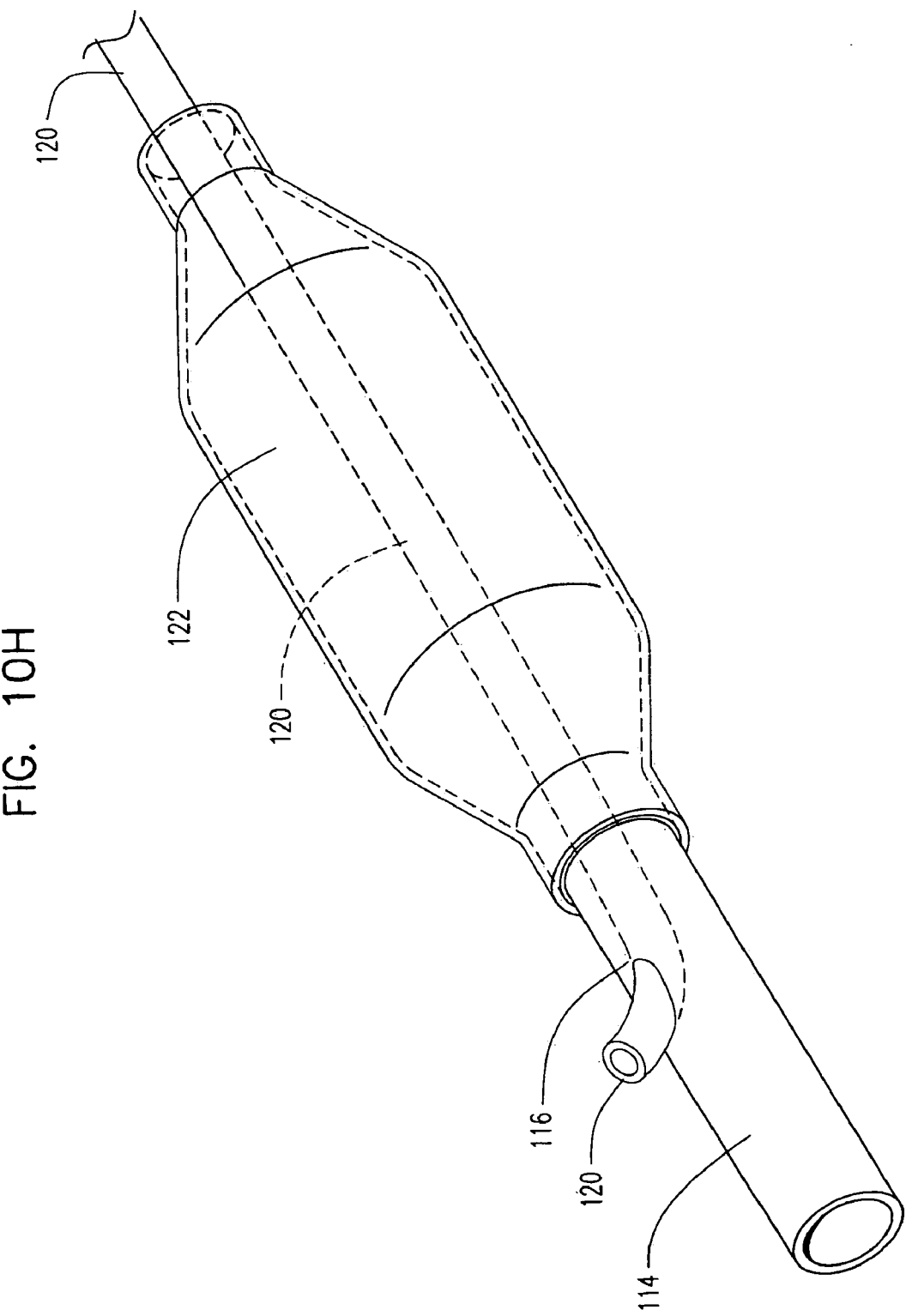

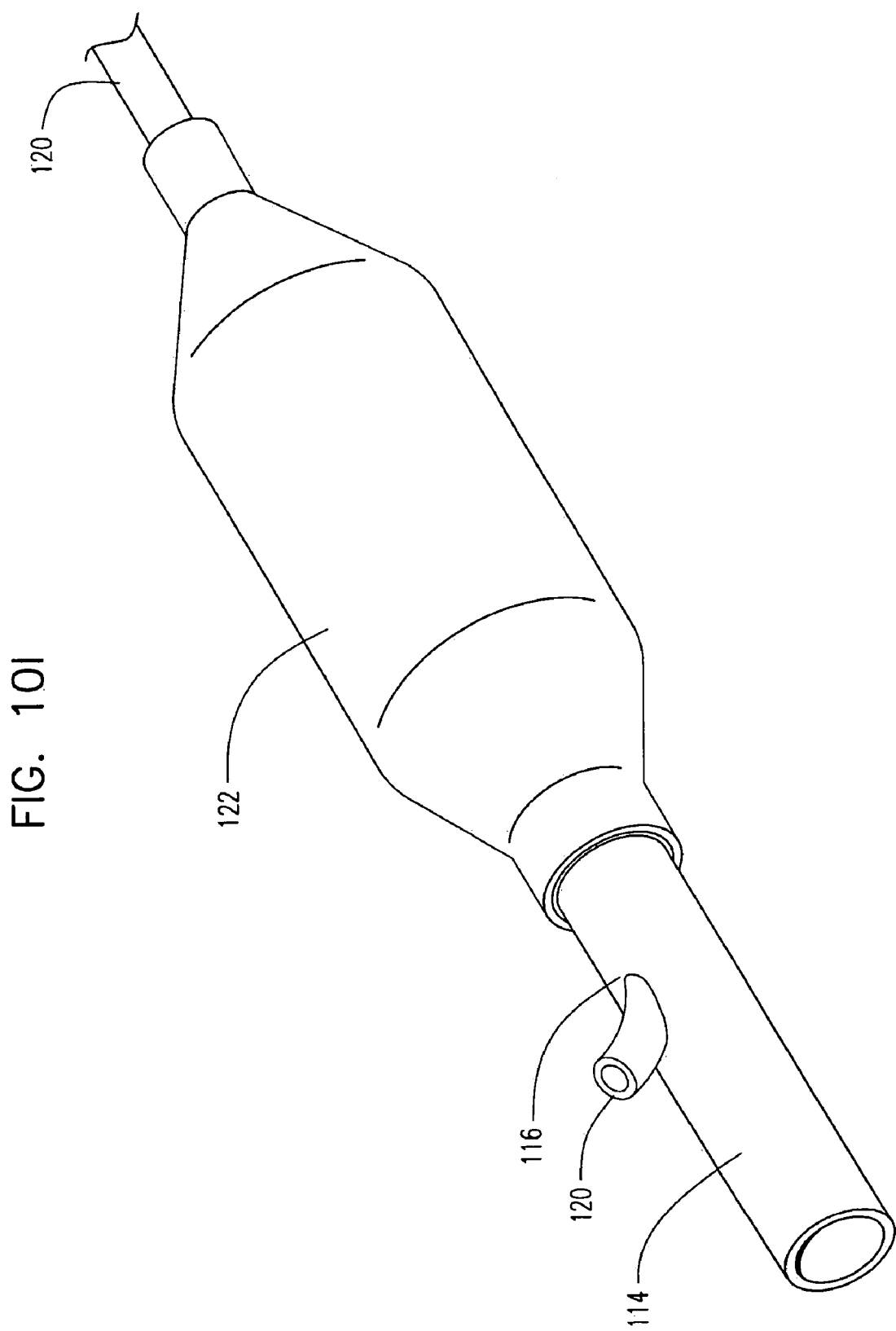

ized for cutting blades, also commonly referred to as atherotomes, which are mounted on medical balloons. Examples of such balloons are described in U.S. Pat. No. 5,545,132, the entire content of which is incorporated by reference herein.

MEDICAL DEVICES FORMED WITH A SACRIFICIAL STRUCTURE AND PROCESSES OF FORMING THE SAME

BACKGROUND OF THE INVENTION

The present invention relates to the field of medical devices, and more particularly to catheters, dilatation balloons, and the like.

Atherosclerotic cardiovascular disease is common, and is caused by a narrowing of the arterial lining due to atherosclerotic plaques. Balloons mounted on the distal ends of catheters are commonly used in the medical treatment of atherosclerotic diseases. Such balloons may be used for dilating lesions or blockages by compressing plaque, for recanalizing and dilating a diseased vessel, and for expanding prosthetic devices such as stents at a desired location in a bodily vessel. The requirements for strength and size of the balloons vary widely depending on the balloon's intended use and the vessel size into which the catheter is inserted.

Percutaneous transluminal coronary angioplasty, or balloon angioplasty, is a non-invasive, non-surgical means of treating peripheral and coronary arteries. This technique consists of inserting an uninflated balloon catheter into the affected artery. Dilation of the diseased segment of artery is accomplished by inflating the balloon which pushes the atherosclerotic lesion outward, thereby enlarging the arterial diameter. The balloon is then deflated and the catheter is withdrawn.

Cutting balloons are another type of medical balloon which have cutting edges, also referred to as atherotomes or blades for recanalizing and dilating a diseased vessel, and facilitating balloon angioplasty procedures.

In any applications such as the above, the balloon traverses a tortuous anatomy as it is being delivered to the location in extremely small bodily vessels and used to open stenoses of blood vessels by balloon inflation, or for delivery of medical devices, for example. In these applications, it is desirable for the balloon to assume as low a profile, i.e. the outer diameter of the balloon, as possible. Considerable effort has been put forth in the development of medical balloons with a low profile by minimizing the dimensions of the shape-form or the inner tube which extends through the balloon to its distal end, and by reducing the wall thickness of the balloon itself.

Several methods have been employed to reduce the profile of the dilatation catheter including manipulating the wall thickness of the balloon material by o developing ever thinner walled balloons, while still retaining the necessary distensibility and burst pressure rating, so as to permit lower deflated profiles.

The profile of the deflated balloon is limited by the thickness of the waist and cone portions of the balloon. Usually, the waist and cone wall thicknesses are thicker than that of the body of the balloon due to the smaller diameter of the waist and cone portions. Thus, a reduction in thickness of the waist and cone portions can reduce the profile.

Balloon forming techniques involve stretching and blowing of the balloon from a segment of extruded polymer tubing. Balloons produced by stretching and blowing a balloon preform or "parison" can have thicker waist and cone walls than the wall thickness of their body portions. It is desirable to reduce the thickness of the cone walls which contribute to the overall thickness of the catheter, to allow for improved tracking, crossing and recrossing of lesions, and to improve refolding after use to facilitate withdrawal of the balloon catheter.

One method of reducing the cone or waist thicknesses of a balloon has been by laser ablating material from the cone or waist. This is disclosed in U.S. Pat. No. 5,826,588, the entire content of which is incorporated by reference herein.

Other methods are disclosed in commonly assigned U.S. Pat. No. 6,193,738, the entire content of which is incorporated by reference herein.

Thus for such applications, thin walled, high strength, relatively inelastic balloons of predictable inflation properties are desired. However, this combination of properties, i.e. thin walls and low resilience, may have increased susceptibility to pin hole formation and ruptures. Stronger balloon materials having greater wall thickness may be employed to increase balloon robustness, but this can also decrease balloon flexibility.

There remains a need for a balloon having improved abrasion resistance and resistance to rupture during use, without sacrificing flexibility, which is not subject to pin holes during the molding process and is readily collapsible to a small diameter upon deflation.

SUMMARY OF THE INVENTION

The present invention relates to medical devices wherein at least a portion of the medical devices are formed using a sacrificial structure, and to processes of forming the same.

Any type of medical device or component thereof, may be formed according to the present invention. Examples include, but are not limited to, catheter shafts, expandable balloons, balloon preforms and the expandable balloons formed therefrom, catheter tips, distal guide wire portions, etc.

While the present invention finds utility for balloons used for coronary angioplasty procedures, the present invention also finds utility for other types of medical balloons including, but not limited to, cutting balloons, balloons used in the biliary duct, urinary tract, balloons employed for the reproductive system, expandable members for medical delivery devices including stents, and so on and so forth.

In one aspect, the invention relates to a process of forming a medical device or component thereof by providing a sacrificial structure which defines at least in part the shape of the medical device or component thereof, providing at least one durable layer which forms at least part of the medical device over the sacrificial structure, and eliminating the sacrificial structure after use.

In some embodiments, the sacrificial structure defines a member for forming a catheter shaft, medical balloon preform, distal end of a guide wire, etc. The sacrificial structure may also define the shape of the expandable balloon member for a catheter assembly, and the durable layer provided over it. The sacrificial structure is eliminated leaving the at least one durable layer which defines the shape of the balloon.

Voids may be provided in the sacrificial structure such that when a durable layer is deposited on the sacrificial structure, the voids are filled by the durable layer. In such an embodiment, the durable layer suitably comprises a polymeric composition.

After applying a first durable layer to the first sacrificial structure, the first sacrificial structure can be removed. The first durable layer may be applied to the inner and/or outer surface of the sacrificial structure. A second durable layer may be applied to the sacrificial structure as well. This second layer may be applied over the first durable layer, or to the opposing surface of the sacrificial structure. The second durable layer may be the same as or different than the first durable layer. Sacrificial layers may be applied between durable layers as well. Furthermore, each sacrificial layer may be manipulated to provide the durable layers which are left with voids, patterns or other surface characteristics therein. These layers may then be eliminated after use.

Other types of materials such as those used for reinforcement such as fibers for example, or micro or nano-particulate materials, can optionally be incorporated into any durable layer, or may be incorporated in between durable layers. These materials can also be incorporated into voids formed in the sacrificial structure, for example, the voids then filled with the composition which forms the durable layer. The resultant structure has fiber reinforcement materials substantially embedded or encapsulated therein.

The present invention may include one, two, three, four or more sacrificial and durable layers. The additional layers may be formed from any materials conventionally employed in the formation of such medical devices including, but not limited to, thermoplastic polymers, thermosetting polymers, biodegradable polymeric materials, fibers, and so forth. Non-polymeric materials may also be employed herein. Any combination of layers may also be employed as will be explained in more detail in the Detailed Description below.

The present invention allows for tailoring of physical properties to the demands of the article being formed. For example, the resultant medical devices can be designed for flexibility, strength, lubricity and for having resistance to abrasions and tearing, e.g. "rip-stop" characteristics.

The present invention also allows for tailoring of physical characteristics of a medical device by manipulating the inner surface of the device. For example, reducing the overall profile of the device by manipulating the internal surface. This allows for leaving a smooth outer surface if that is so desired.

Other aspects of the invention are described in the Detailed Description and in the claims below.

BRIEF DESCRIPTION OF THE DRAWINGS

FIGS. 2A-2G are perspective views of a process of making the tubular member similar to that shown in FIG. 2A according to the invention.

FIG. 3 is a perspective view of a balloon according to the invention.

FIGS. 4A-4C illustrate an embodiment of a process for forming a balloon preform according to the invention.

FIGS. 5A-5F illustrate a process of making a balloon preform according to the invention.

FIGS. 7A-7D illustrate an embodiment of the invention whereby fibers are embedded in the wall of a dilatation balloon.

FIGS. 8A-8F illustrate an embodiment of the present invention whereby the distal sensor pocket of an intravascular ultrasound catheter assembly is formed.

FIGS. 10A-10I illustrate an embodiment of the present invention whereby a guide wire port for a rapid exchange catheter assembly is created.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

Some embodiments of the present invention are directed to processes for forming medical devices, especially those deployed and operated through various body lumens including, for example, vascular channels, and to devices obtained from such processes.

Figure 1:
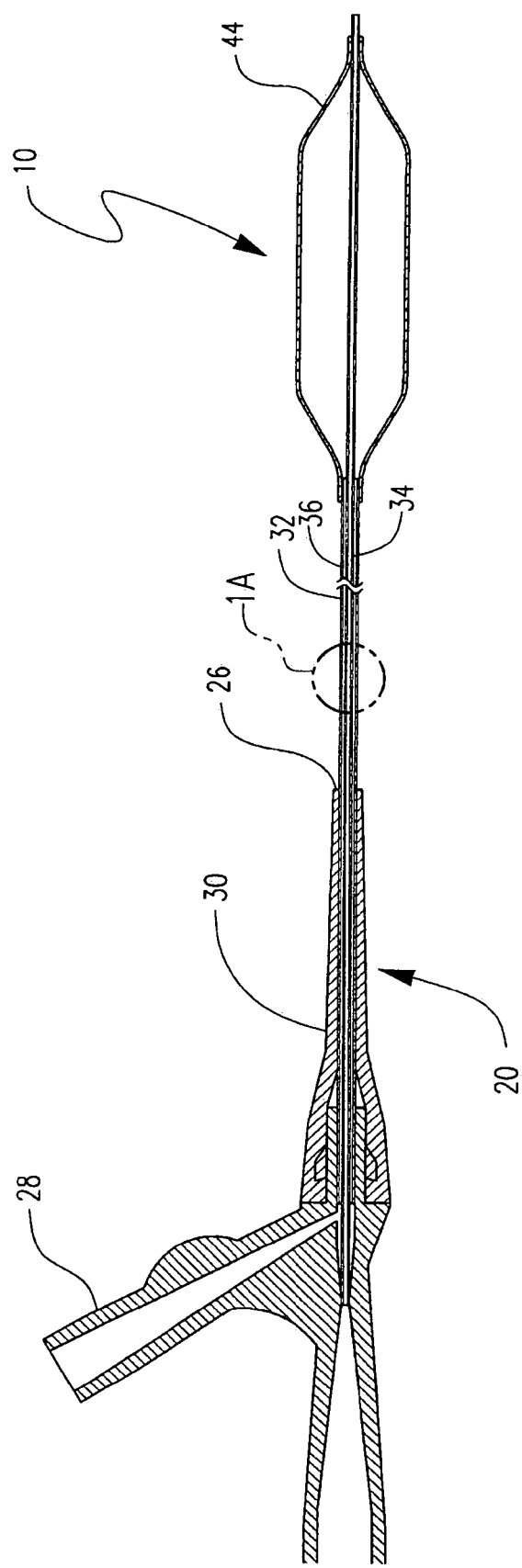
FIG. 1 is a longitudinal cross-sectional side view of a catheter assembly having a balloon of the present invention mounted thereon.

Referring now to the figures, FIG. 1 shows balloon 10 in combination with a catheter assembly 20. Balloon 10 may be formed in a number of ways using a sacrificial structure (not shown) according to the invention, several embodiments of which are explained in detail below, and wherein the balloon includes at least one durable layer 44 which forms at least a part of the balloon structure. In this embodiment, durable layer 44 defines the shape of the balloon structure. The durable layer may comprise any suitable polymeric composition.

Figure 1A:
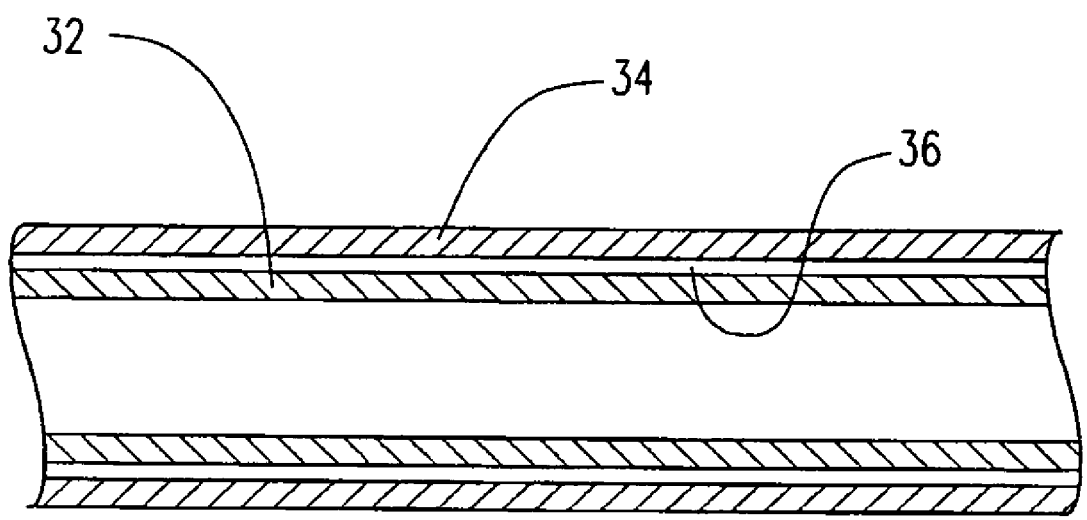
FIG. 1A is an enlarged view taken at section 1A in FIG. 1.

Catheter 20 is a representative simple over-the-wire (OTW) or single-operator-exchange (SOE) angioplasty balloon catheter according to the invention. Such balloon catheters are discussed, for example, in commonly assigned U.S. Pat. Nos. 6,113,579, 6,517,515 and 6,514,228 each of which is incorporated by reference herein in its entirety. In this embodiment, catheter 20 has an elongate shaft assembly 26 and a conventional OTW-type manifold assembly 28 connected to proximal end of shaft assembly 26. Manifold assembly 28, is further shown with a strain relief 30. The shaft assembly 26 includes an outer tube 34 coaxially disposed about inner tube 32 which defines a guide wire lumen 36 as shown in enlarged view in FIG. 1A, taken at section 1A in FIG. 1. This is only an illustration of such a catheter assembly and is not intended to limit the scope of the present invention. Numerous structures are known to those of skill in the art, any of which may be employed herein.

While the embodiments which follow are directed to the formation of tubular members, it will be appreciated that non-tubular medical articles can also be formed.

Balloon 10 shown in FIG. 1, may be formed using any techniques known in the art, such as by directly molding the balloon structure, or by first forming a balloon preform or parison, and then processing the preform according to known techniques such as by gas pressure molding, for example, into an expandable balloon member. Balloon 10 may also be formed according to the invention s further described below.

For the formation of a variety of articles according to the invention, a tubular member may first be formed. Tubular members may be used for catheter shafts, catheter tips, distal portions of guide wires, etc.

The present invention can be used to form medical devices or components thereof in a variety of ways. The medical devices or components thereof may take on a variety of configurations as described in detail below.

Figure 2A:
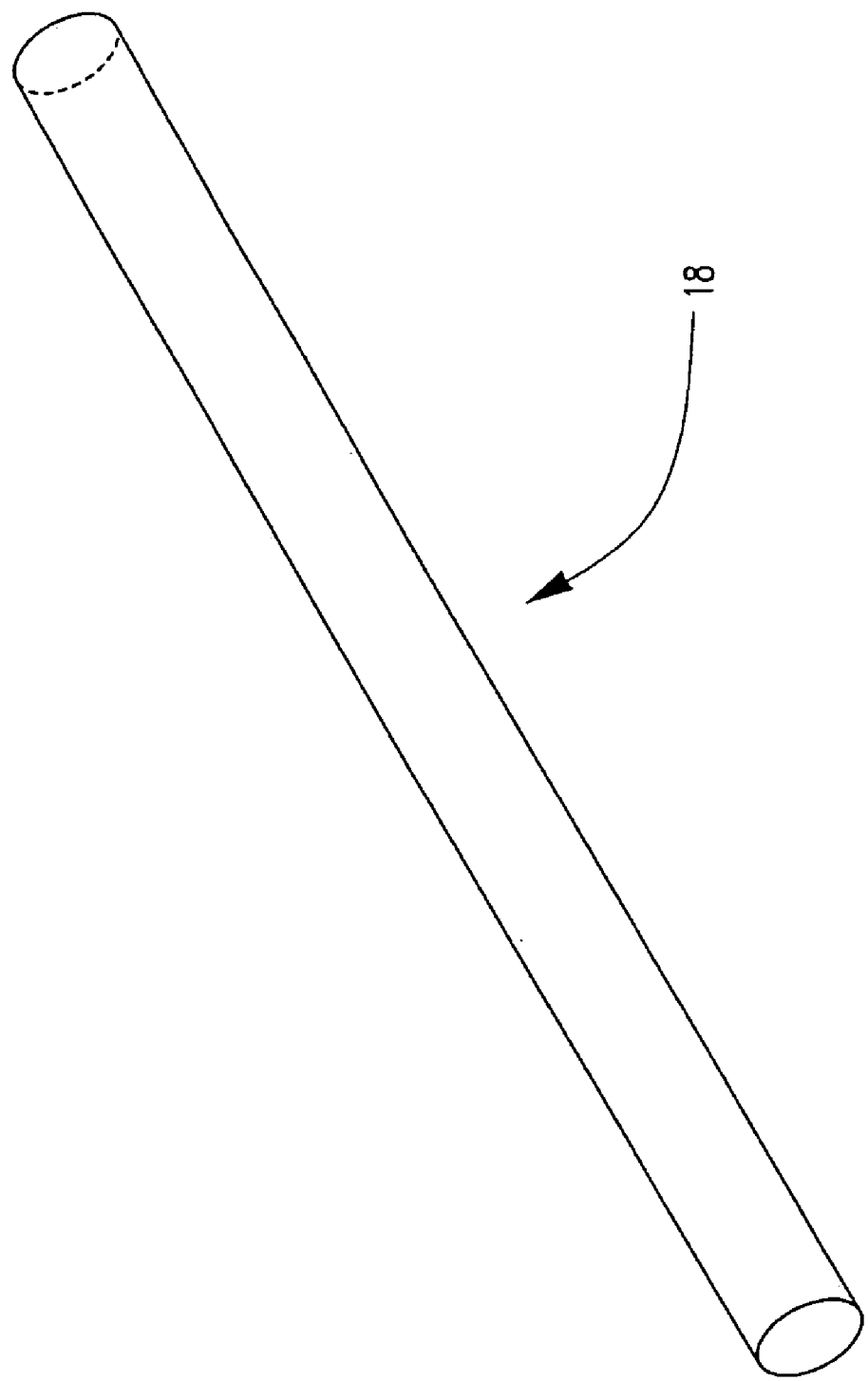
Figure 2B:
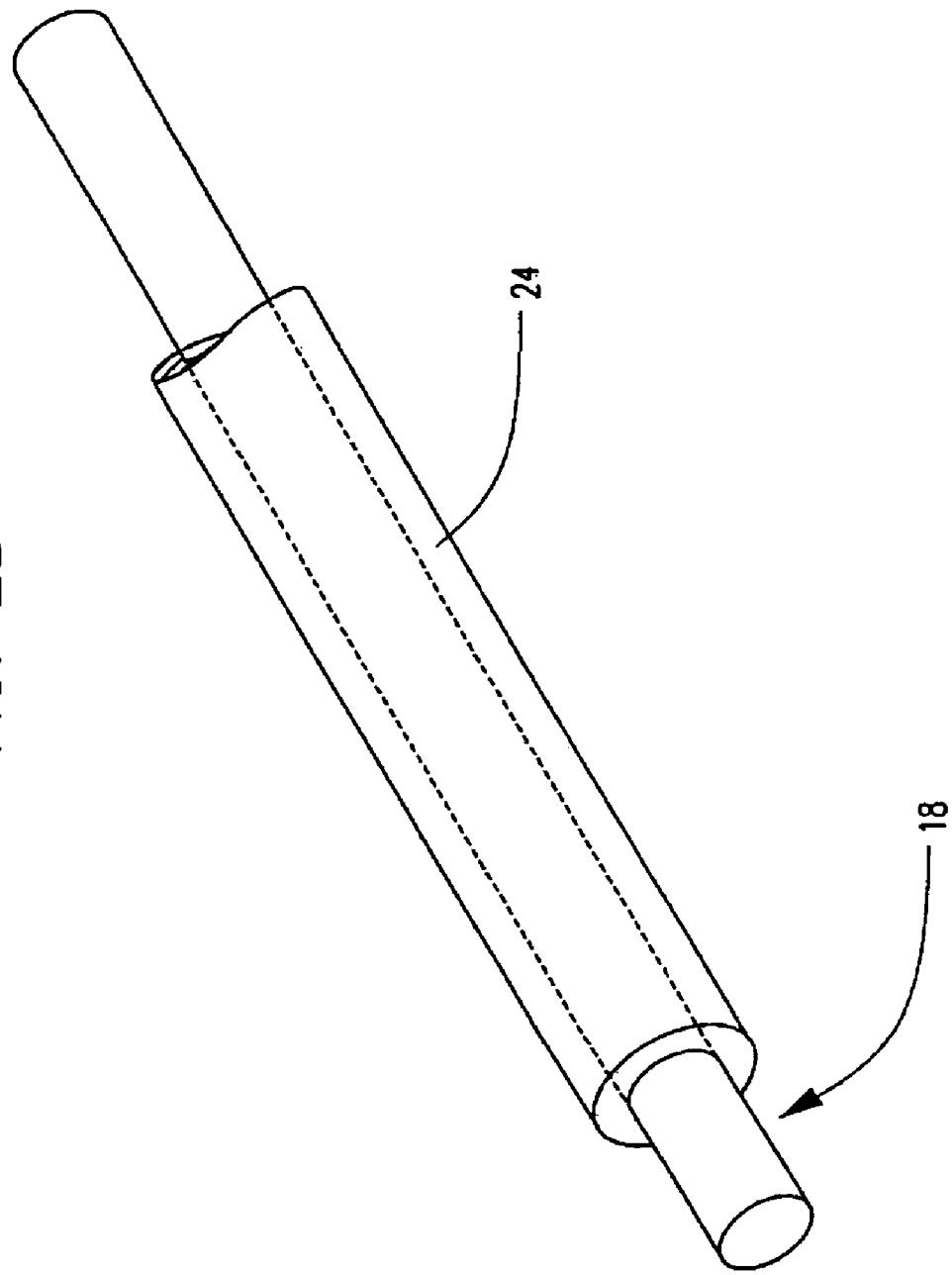

FIGS. 2A-2G illustrative one method of forming a member in accordance with the invention. In this embodiment, a mandrel 18 as shown in FIG. 2A is employed. Sacrificial structure 24 is provided over mandrel at as shown in FIG. 2B.

In other embodiments described below, the process may start with a sacrificial structure which defines the shape of at least a portion of a medical device or component thereof, rather than a mandrel.

Mandrel 18 may be formed from any suitable material known in the art including both metals and rigid polymeric compositions. In this embodiment, mandrel 18 is formed from a durable material. Mandrel 18 is typically removed after use. Examples of suitable materials include, but are not limited to, metals such as copper, rigid polymers including fluoropolymers such as polytetrafluoroethylene (PTFE) available under the tradename of Teflon®, acetal polymers, etc. In one embodiment, silver plated copper is employed.

As used herein sacrificial materials include those which may be eliminated from the resultant tubular member by melting, dissolution, and so forth. Dissolution does not require complete dissolution, but rather may involve partial dissolution sufficient for removal of the shape-form from the article.

Examples of sacrificial materials include, but are not limited to, ice, starch, sugar, waxes, solvatable polymeric materials including those which are dispersible or soluble in water such as polyvinyl alcohol (PVOH), polyvinyl acetate (PVA), and so forth. Specific PVA polymers may be purchased from Adept Polymers Limited, Unit 7, Woodrow Way, Fairhills Industrial Estate, Irlam, Manchester, M44 6ZQ under the name of Depart Products, W-50 product series. One such polymer has a melting temperature as measured by DSC at 206° C. Dissolution may be partial, providing that the material is reduced to a size which is small enough such as to be readily removable from the preform or balloon structure. Some non-limiting examples of suitable sacrificial shape-forms are described in commonly assigned, copending patent application Ser. No. 10/622,621, the entire content of which is incorporated by reference herein in its entirety.

The sacrificial structure 24 may be provided over the mandrel 18 using any method known in the art including, but not limited to, overcoating, extruding, painting, dipping, spraying, and so forth.

The sacrificial structure 24 can be manipulated to provide specific features to the resultant medical device. For example, channels, slits, indentations, or other types of voids can provided to the surface of the medical device by ablating, grinding, cutting or other wise removing material from the sacrificial structure 24. Providing such characteristics in the sacrificial structure 24 can provide surface characteristics in the durable layer after the sacrificial structure 24 has been removed. For example, voids in the sacrificial structure 24 result in protuberances in the durable layer, or ultimately, in the medical device. The sacrificial structure 24 may be removed using any means suitable for the type of material from which it is formed, and the invention is not limited to those listed above. Shown in FIG. 2C, a radial section 38 of sacrificial structure 24 has been completely removed. The areas indicated by reference numeral 43, are those which have not been further manipulated. The sacrificial structure 24 may also be only partially removed to form a channel 40 also shown in FIG. 2C.

Alternatively as shown in FIG. 2D, sections of sacrificial structure 24 may be completely removed in one region as shown at 38 and only partially removed in another region as shown at 42, with no material having been removed from regions 43 of the sacrificial structure 24.

After manipulation of sacrificial structure 24, a durable layer 44 may be applied over sacrificial structure 24 as shown in FIG. 2E.

As used herein, the term "durable layer" is used to describe a layer(s) which forms at least a part of the medical device member. Durable layer 44 may comprise any suitable thermoplastic and/or thermosetting material for formation of medical devices. Thermosetting materials include those cured through additive induced, i.e. chemically induced, and/or heat or radiation induced cross-linking. Thermosetting materials include, for example, one and two part curing systems, moisture cures, radiation cures, etc. Thermoset materials may also include polymers, pre-polymers, oligomers, and monomers. Curable compositions are disclosed in commonly assigned copending U.S. patent application Ser. No. 10/622,621, which has been previously incorporated by reference herein, above.

As will be shown in embodiments discussed below, durable layer 44 may also include fibers. Fibers are thread-like materials which can be in the form of a monofilament, i.e. a single thread, or in multifilament forms, i.e. a yarn, and the present invention is not limited to any particular fiber form. For example, fibers may be in the form of a web, mat, yarn, braid, weave, rove, chopped, etc. The fibers may be positioned randomly, or may be positioned uniformly. If the article being made is a balloon preform, the fibers may be positioned such that they are on the body, waist or cone portions of the balloon, or any combination thereof.

Suitable fibers for use herein include both synthetic and natural fibers. As used herein, natural fibers refer to those which occur in nature, e.g. those produced by members of the phylum Arthropoda including arachnids and insects such as spiders, silk worms, black flies, wasps, and lacewing flies.

Other suitable natural fibers include, but are not limited to, cotton, wool, help and jute.

Synthetic fibers refer to those fibers which are man-made such as synthetic polymeric fibers, and those produced using recombinant protein technology.

Examples of suitable synthetic high strength polymeric fiber materials include, but not limited to, such as poly-par-aphenylene terephthalamide fibers available from DuPont de Nemours & Co. under the tradename of Kevlar®; liquid crystal polymer fibers such as those available from Celanese Chemicals in Dallas, Tex. under the tradename of Vectran®; ultra high strength polyethylene fibers such as those available from Honeywell International in Morristown, N.J. under the tradename of Spectra® and from Toyobo Co., Ltd. in Osaka, Japan under the tradename of Dyneema®; polyester fibers such as those available from Invista in Wichita, Kans. under the tradename of Dacron®; poly-(p-phenylenebenzobisthia-zole) (PBT) fibers such as Terlon® (PBT), the "know-how" and the technical documentation for manufacturing which is offered by license from Russian Federation, 141009, Mytis-chi, Moscow Region, VNIIPV; rigid-rod chain molecules of poly(p-phenylene-2,6-benzobisoxazole) (PBO) available from Toyobo Co., Ltd. under the tradename of Zylon®, poly-imide (PIM), etc.

The above lists are intended for illustrative purposes only, and not intended to limit the scope of the present invention.

Fibers are discussed in U.S. Pat. No. 6,746,425, and in commonly assigned U.S. application Ser. No. 10/862,250, the entire content of which is incorporated herein by reference.

The use of fibers is not limited to any particular embodiment, and may be employed in any of the embodiments disclosed herein.

The fibers may be applied to a mandrel, to the sacrificial structure or to the durable layer of the device. The durable layer 44 may fill the voids 38 created by removal of the material from sacrificial structure 24 such that the resultant durable layer 44 left after removal of the sacrificial structure 24 has the desirable characteristics.

Suitable thermoplastic and/or thermosetting polymeric materials, including both elastomeric and non-elastomeric materials may be employed in forming the composition of the durable layer.

Thermosetting materials useful herein are disclosed in commonly assigned copending patent application Ser. No. 10/622,621, the entire content of which is incorporated by reference herein in its entirety.

Thermoplastic materials find particular utility herein for use in the composition of the durable layer. Examples of non-elastomeric materials include, but are not limited to, polyolefins including polyethylene and polypropylene, polyesters, polyethers, polyamides, polyurethanes, polyimides, and so forth, as well as copolymers and terpolymers thereof. As used herein, the term "copolymer" shall hereinafter be used to refer to any polymer formed from two or more monomers.

Examples of suitable elastomeric materials include, but are not limited to, elastomeric block copolymers including the styrenic block copolymers such as styrene-ethylene/butylene-styrene (SEBS) block copolymers disclosed in U.S. Pat. No. 5,112,900 which is incorporated by reference herein in its entirety. Other suitable block copolymer elastomers include, but are not limited to, styrene-isoprene-styrene (SIS), styrene-butadiene-styrene (SBS), styrene-isobutylene-styrene (SIBS), styrene-ethylene/propylene-styrene (SEPS) and so forth. Block copolymer elastomers are also described in commonly assigned U.S. Pat. Nos. 6,406,457, 6,171,278, 6,146,356, 5,951,941, 5,830,182, 5,556,383, each of which is incorporated by reference herein in its entirety.

Elastomeric polyesters and copolyesters may be employed herein. Examples of elastomeric copolyesters include, but are not limited to, poly(ester-block ether) elastomers, poly(ester-block-ester) elastomers and so forth. Poly(ester-block-ether) elastomers are available under the tradename of HYTREL® from DuPont de Nemours & Co. and consist of hard segments of polybutylene terephthalate and soft segments based on long chain polyether glycols. Such polymers are also available from DSM Engineering Plastics under the tradename of ARNITEL®.

Non-elastomeric polyesters and copolymers thereof may be employed such as the polyalkylene naphthalates including polyethylene terephthalate and polybutylene terephthalate, for example.

Polyamides including nylon, and copolymers thereof may be employed herein. Block copolymer elastomers such as poly(ether-block-amides) may be employed herein and are available from Atofina Chemicals in Philadelphia, Pa., under the tradename of PEBAX®.

The choice of material will depend on the final use to which the medical device member will be put. Catheter shafts, for example, may be formed from a different polymeric composition than a catheter balloon, and the catheter balloon later disposed about the shaft, although catheter assemblies may be formed as a one-piece unit as well. The selection may also be based on the end use of the balloon as well. Angioplasty balloons, for example, may be formed from a different polymeric composition than a cutting balloon.

For examples of suitable balloon materials see commonly assigned U.S. Pat. Nos. 5,549,552, 5,447,497, 5,348,538, 5,550,180, 5,403,340, 6,328,925, each of which is incorporated by reference herein in its entirety. Some specific examples of suitable balloon materials include, but are not limited to, polyalkylene terephthalates and polyamide copolymers such as polyethylene terephthalate, polybutylene terephthalate, and polyether-block-amides, for example.

The above lists are intended for illustrative purposes only, and not as a limitation on the scope of the present invention. Other polymeric materials not described herein, may find utility in the formation of catheter balloons according to the invention.

The steps above can be repeated to achieve a medical device member having a desired wall thickness. For example, as indicated above, over sacrificial structure 24 is provided the first durable layer. A further sacrificial layer may be deposited onto the a first durable layer, and a second durable layer deposited onto the sacrificial layer and so on and so forth, and not necessarily in that order. Furthermore the first durable layer may be provided directly on mandrel followed by sacrificial structure. Such embodiments are discussed in more detail below.

The mandrel 18 may then be removed leaving the structure as shown in FIG. 2F wherein the sacrificial structure 24 in this embodiment, is still present. Sacrificial structure 24 can be eliminated by melting or by flushing with solvent depending on the polymeric material selected for use leaving the final structure shown in FIG. 2G. The final structure is defined by the durable layer 44. PVOH is readily dissolved with water at temperatures from about 25° C. to about 110° C., and is only one example of a material which may be employed in this embodiment.

A member formed by such a process as described in FIGS. 2A-2G may be suitably employed as a balloon preform shown at 12 in FIG. 2G, which may be employed to form an expandable balloon.

Any suitable balloon forming techniques may be employed. Such techniques are known in the art. An example of one method is described in U.S. Pat. No. 4,490,421 to Levy which is incorporated by reference herein in its entirety.

One method involves placing a balloon parison formed by the process described above, in a balloon mold and expanding the parison into the desired balloon configuration in the balloon mold. The main processing steps may include other steps therein such as stretching and radial orientation of the balloon material, for example, as well as annealing and heat setting.

Shown in FIG. 3 is a conventional dilatation balloon 10 having waist 52, cone 54 and body 56 portions. One concern when molding such balloons from a balloon lesser degree than the body portions, resulting in cone and waist portions of greater wall thickness than the body. This can be a concern with expandable medical balloons, particularly in the cone region, for ease of deflation and rewrap of the balloon after use.

According to one embodiment of the invention, the member 12 formed according to the process illustrated in FIGS. 2A-2G, after removing the mandrel 18 and sacrificial structure 24 (see FIGS. 2F and 2G), can be used as a balloon preform and can be further processed using conventional balloon forming techniques such as by gas pressure molding, to form dilatation balloons having cone portions of lesser wall thickness for better deflation and rewrap characteristics. The resultant balloon preform 12, shown in FIG. 2G provides a central region 38 which has a greater wall thickness and may become body portion 56 of balloon 10 shown in FIG. 3, thus providing a molded balloon wherein the wall thickness of the body is closer to the thickness of the cones and waist after molding.

Figure 4C:
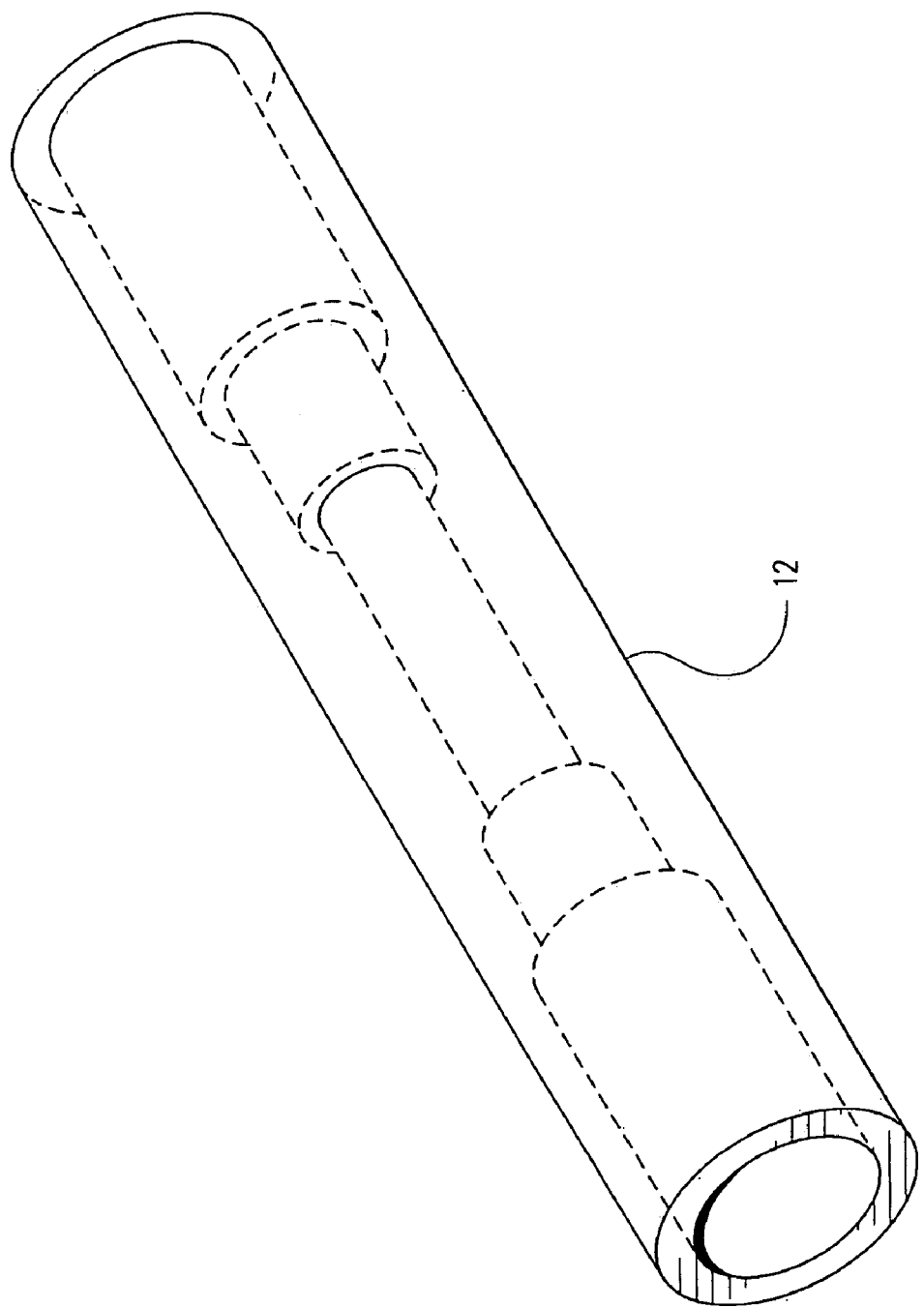

The above process can also be employed to form an alternative preform structure having a stepped inner profile as shown in FIG. 4A. In this embodiment, regions 64 and 66 of sacrificial structure 24 may be ablated to remove material. Less material is removed from region 64 than from region 66. No material is ablated from region 62. A durable layer 44 is then provided over sacrificial structure 24 as shown in FIG. 4B. A perspective view of the resultant balloon preform 12 which has a stepped inner profile after removal of sacrificial structure 24 is shown in FIG. 4C.

Figure 5B:
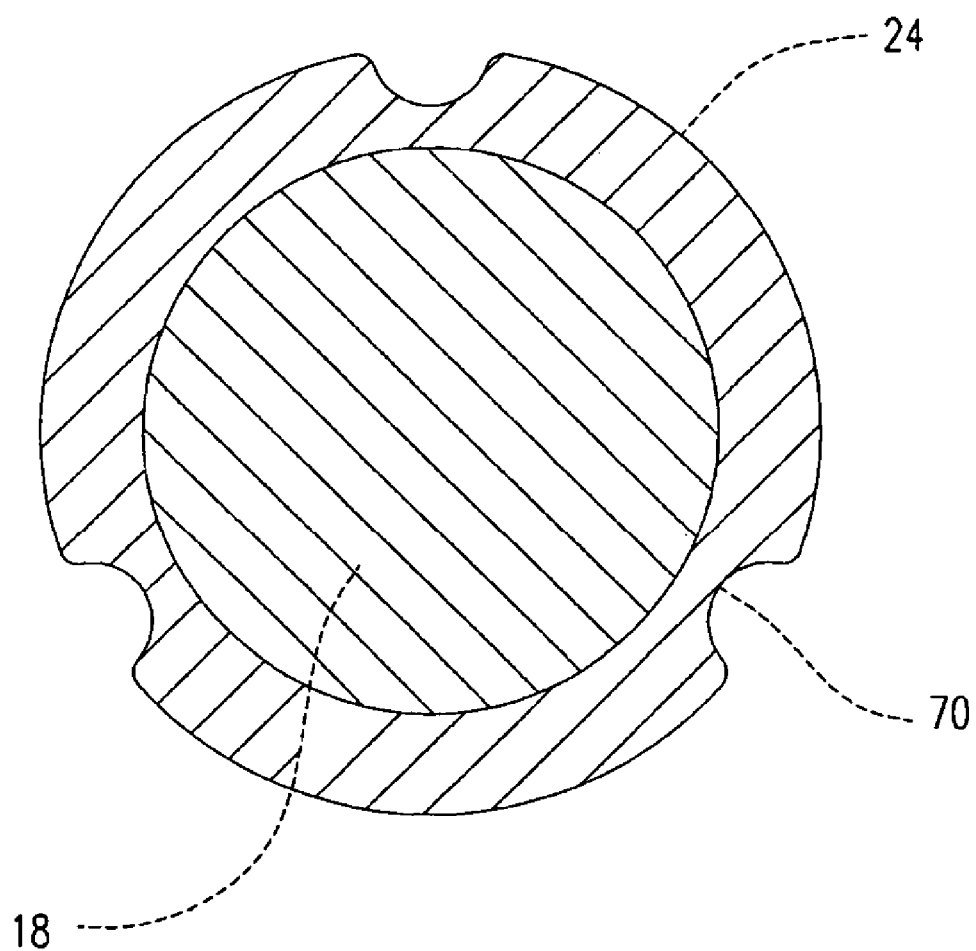
Figure 5D:
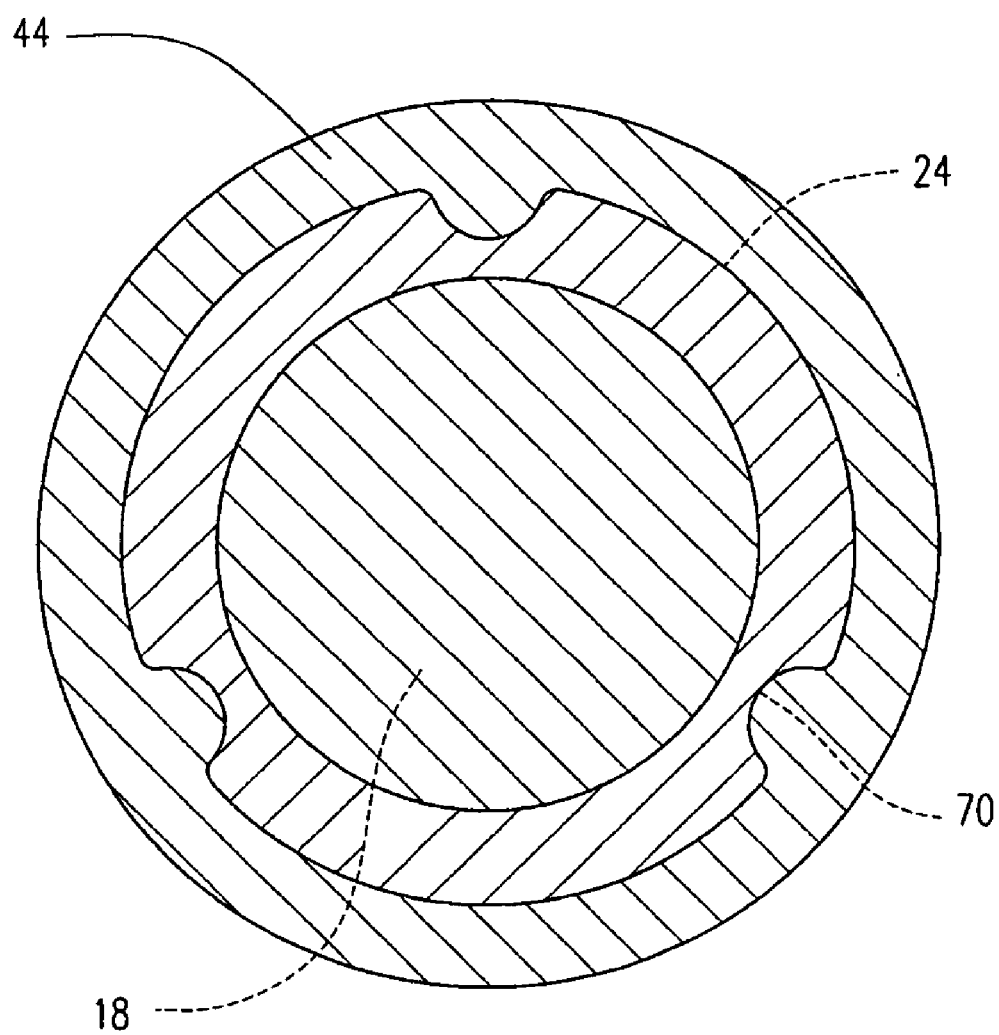

In another embodiment, a structure 24 comprising a polymeric material such as PVA or PVOH is applied over a mandrel as previously depicted in FIG. 2C. As discussed above, any polymeric material may be employed provided it is readily eliminated after the desired member has been formed. Voids 70 are provided in the sacrificial structure 24 as shown in FIG. 5A. The voids 70 may be produced in the sacrificial structure 24 using any suitable method. One preferable method is laser ablation, but other methods including grinding, cutting, and so forth, may be employed as well as discussed above. FIG. 5B is a cross-sectional view showing the voids in sacrificial structure 24. A durable polymeric layer 44 may then be provided over the sacrificial structure 24 as shown in FIG. 5C. A cross-sectional depiction is shown in FIG. 5D. The mandrel 18 may removed at any time after the sacrificial structure 24 has been applied to the mandrel. It may be desirable to remove the mandrel 18 after application of the durable layer 44, however, this is not necessary. The sacrificial structure 24 may be removed after removal of the mandrel 18 and after application of the durable layer 44 using appropriate means. If sacrificial structure 24 is formed with a water dispersible or soluble polymer such as PVA or PVOH, employing a water flush at a temperature between about 25° C. and about 110° C., readily eliminates sacrificial structure 24.

Figure 5F:
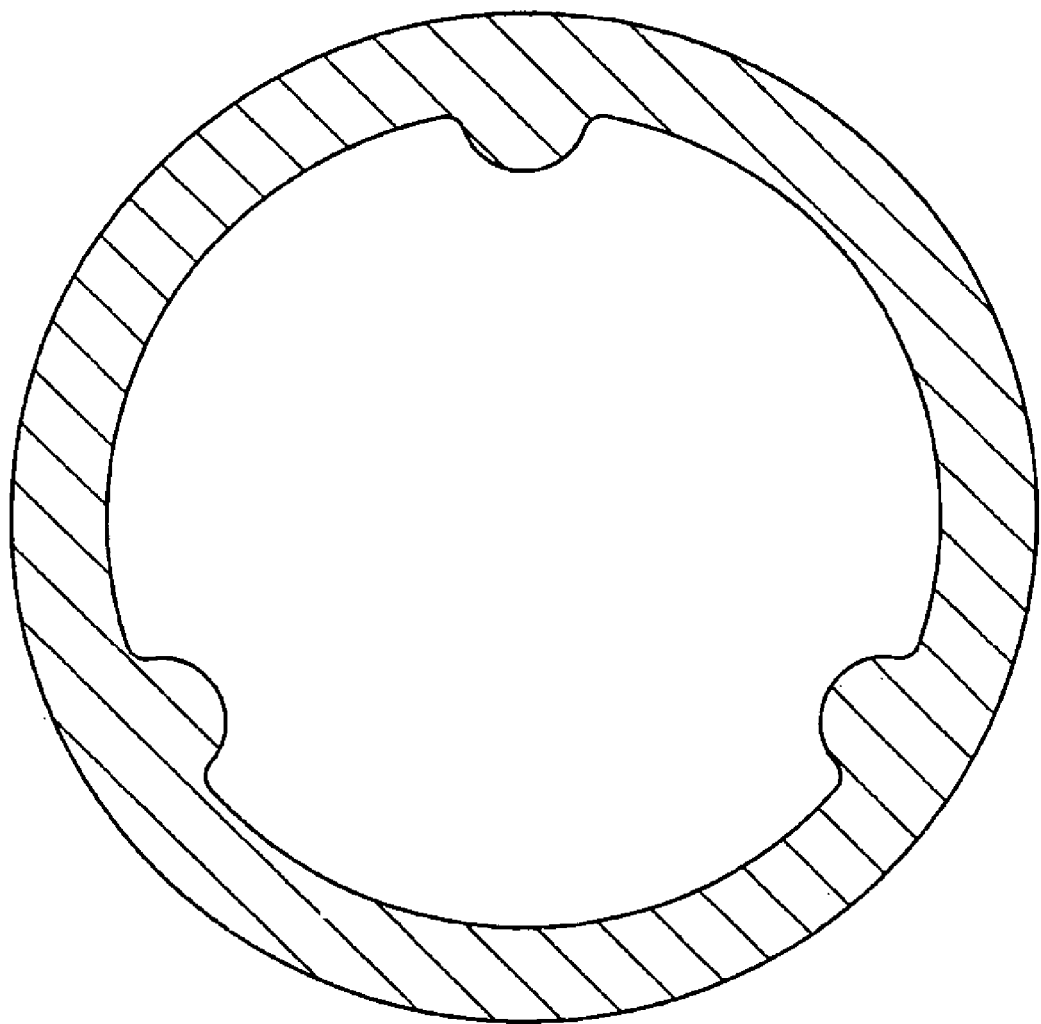

FIG. 5E is a longitudinal cross-sectional view of a balloon preform 12', which has been formed by the method described in FIGS. 5A-5D. The balloon preform exhibits projections 72 on the inner surface 73 of the durable layer 44 which defines the balloon preform 12'. Projections 72 project inward toward lumen 75 of balloon preform 12'. FIG. 5F is a radial cross-sectional view of the preform 12' of FIG. 5E.

Figure 6A:
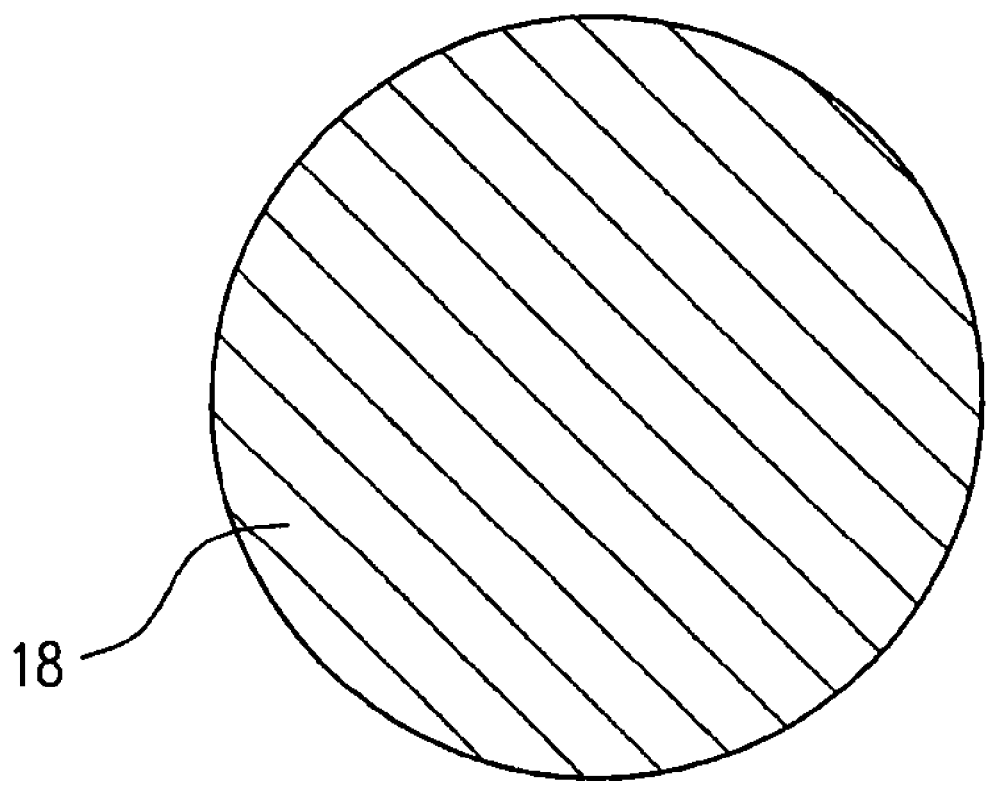
FIGS. 6A-6G illustrate a process whereby channels may be produced in a balloon preform.
Figure 6B:
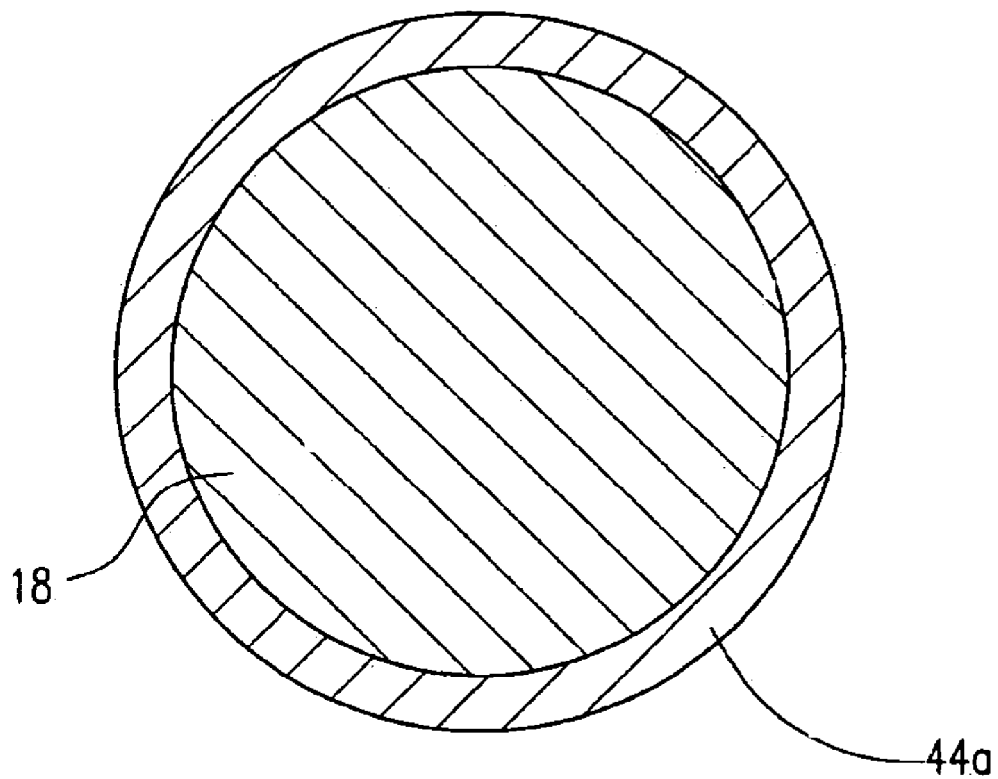
Figure 6C:
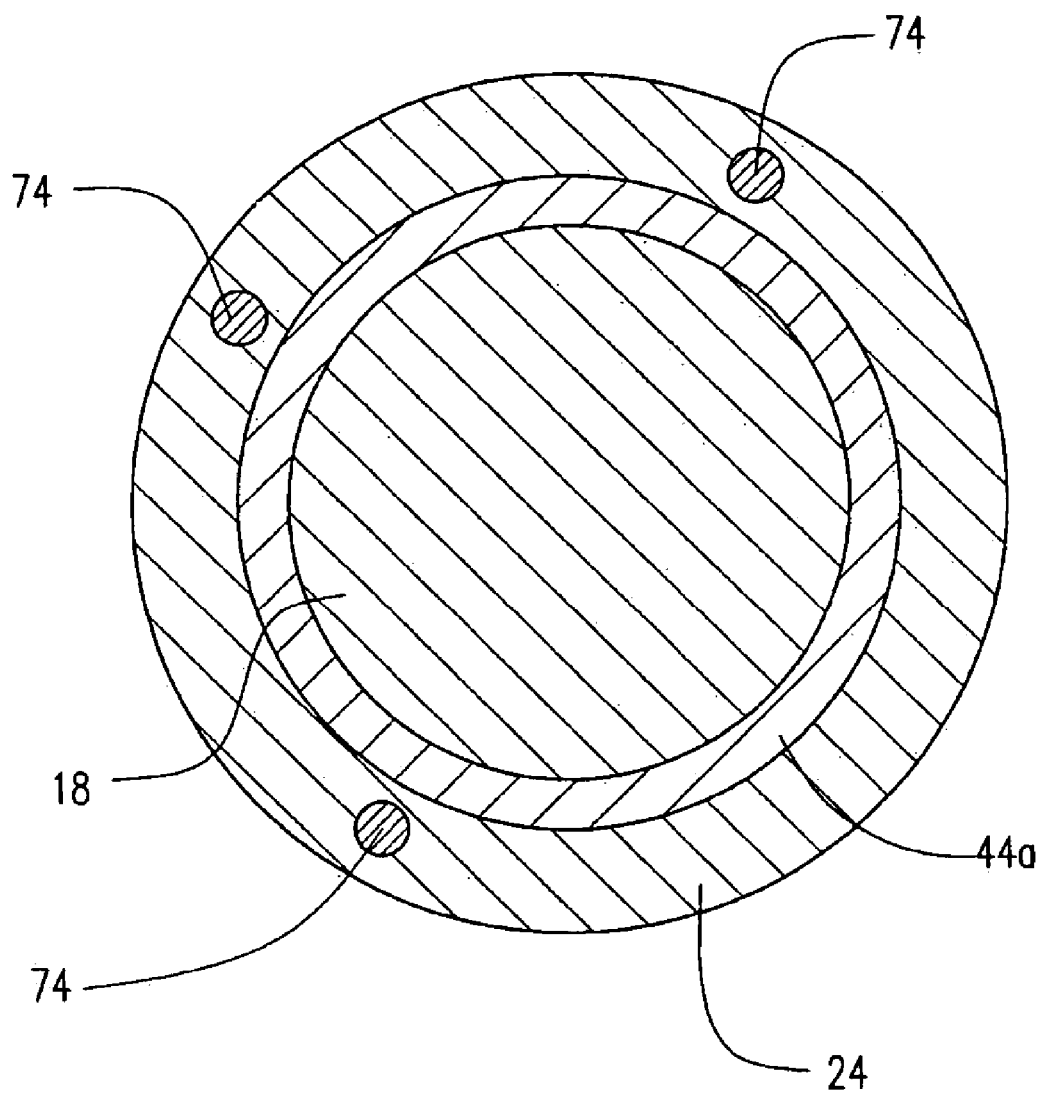
Figure 6D:
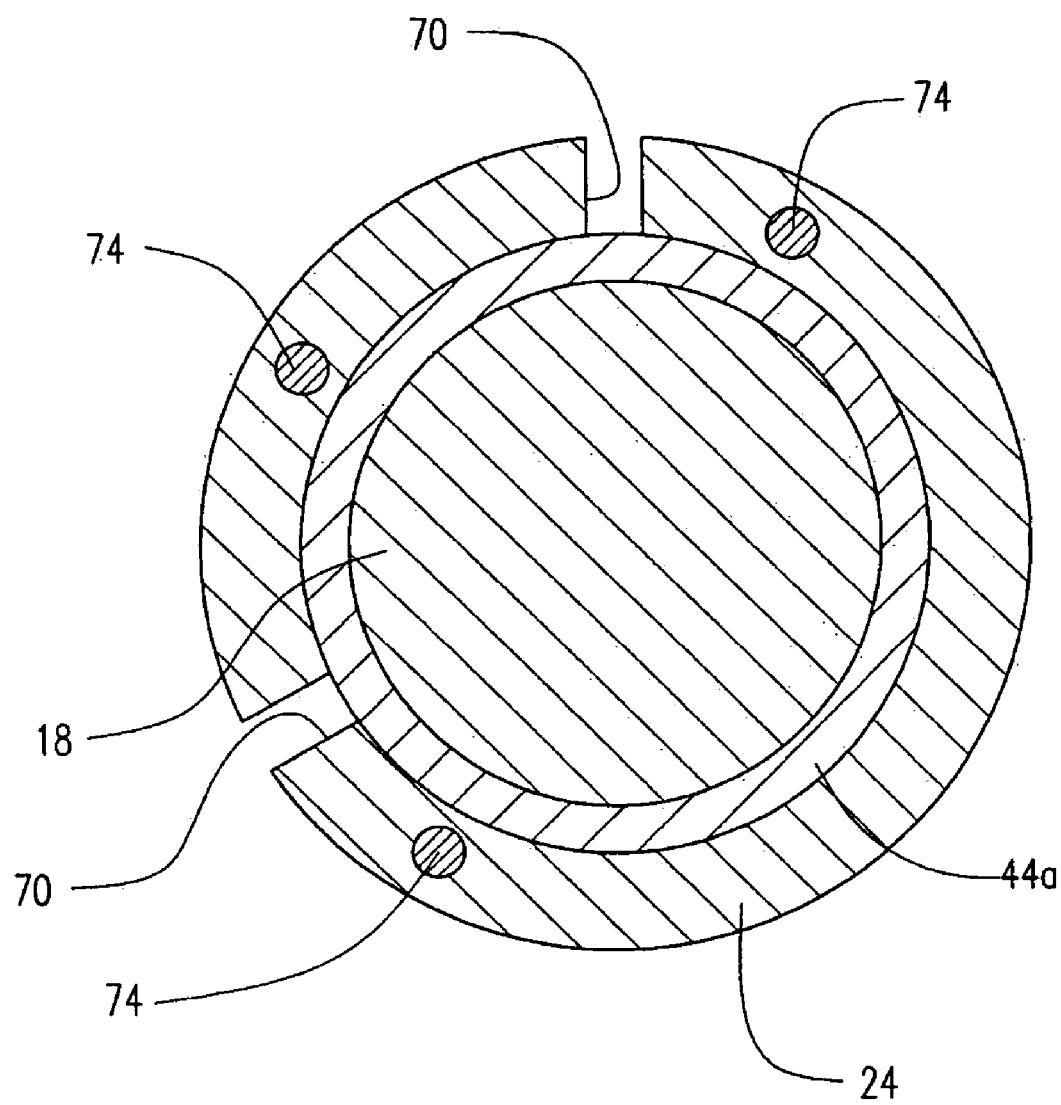

FIGS. 6A-6G illustrate another method whereby a member for a medical device is formed according to the invention. The method is illustrated by use of radial cross-sectional depictions of each step conducted in the formation of the article. FIG. 6A is a radial cross-section of mandrel 18. A first durable layer 44a is provided over mandrel 18 as shown in FIG. 6B such as by extrusion or other suitable method. A sacrificial structure 24 is provided over first durable layer 44a as shown in FIG. 6C. The sacrificial structure 24 may be extruded over durable layer 44a and has members or wires 74 extending therethrough. The wires 74 may be in the form of metal or polymeric wire such as those formed from nylon, polyester, and so forth, and any number from one wire or more may be employed. First sacrificial structure 24 may be provided over first durable layer 44a simultaneously through the use of coextrusion techniques, or as a sequential step. Voids or notches 70 are provided in the first sacrificial structure 24 using any suitable method such as by laser ablation or other technique, and may be provided either radially or longitudinally in the structure 24 as shown as shown in FIG. 6D.

Figure 6E:
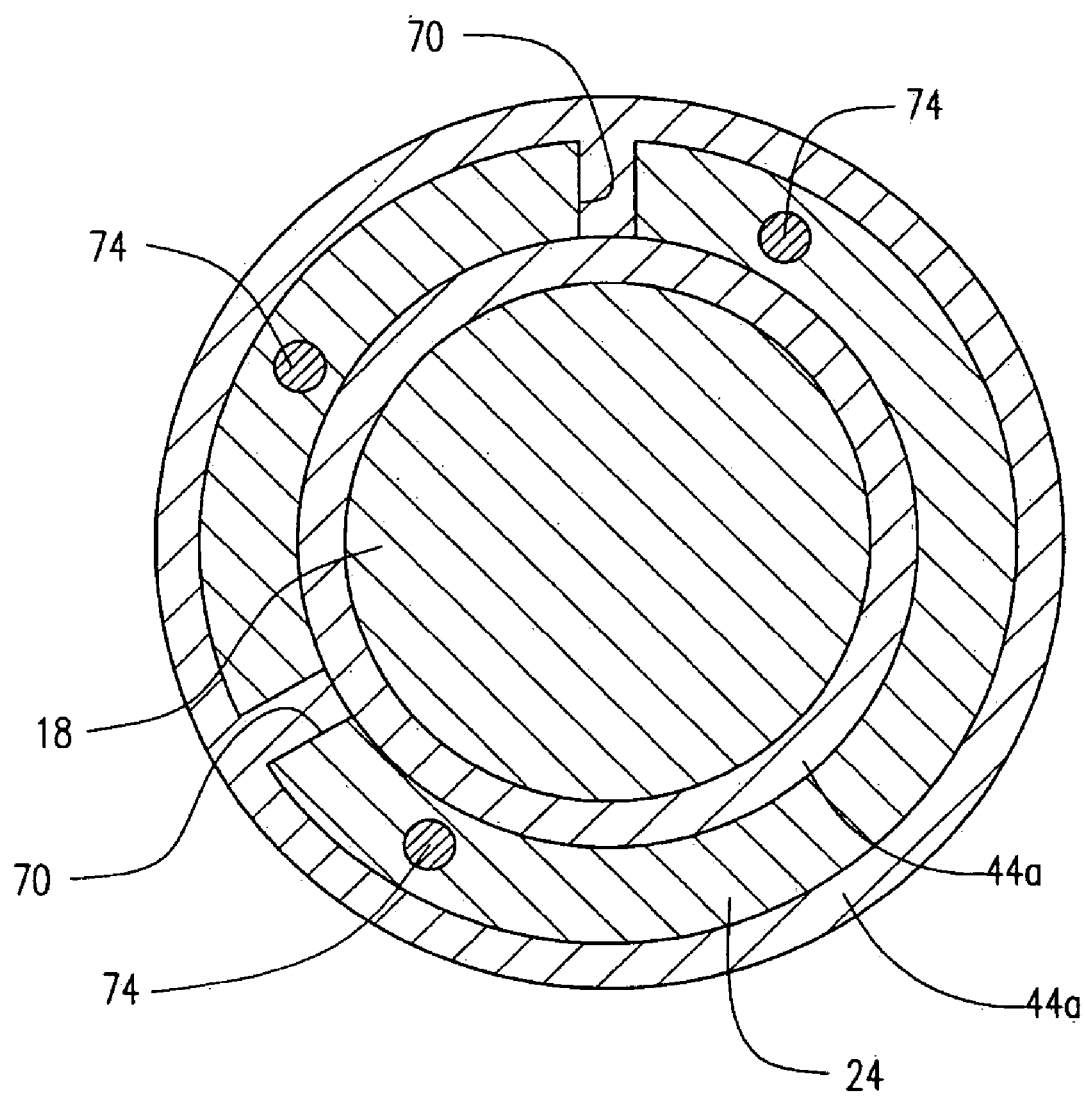
Figure 6F:
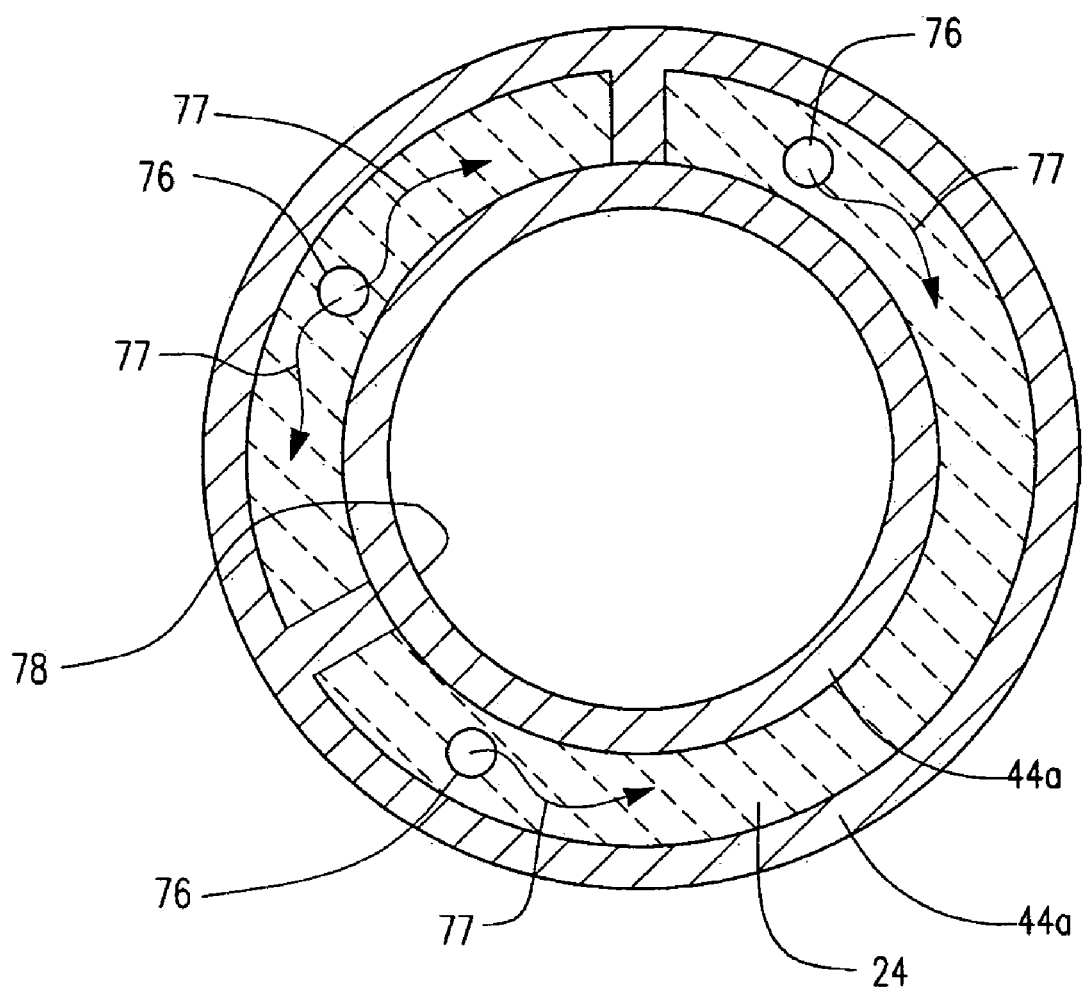
Figure 6G:
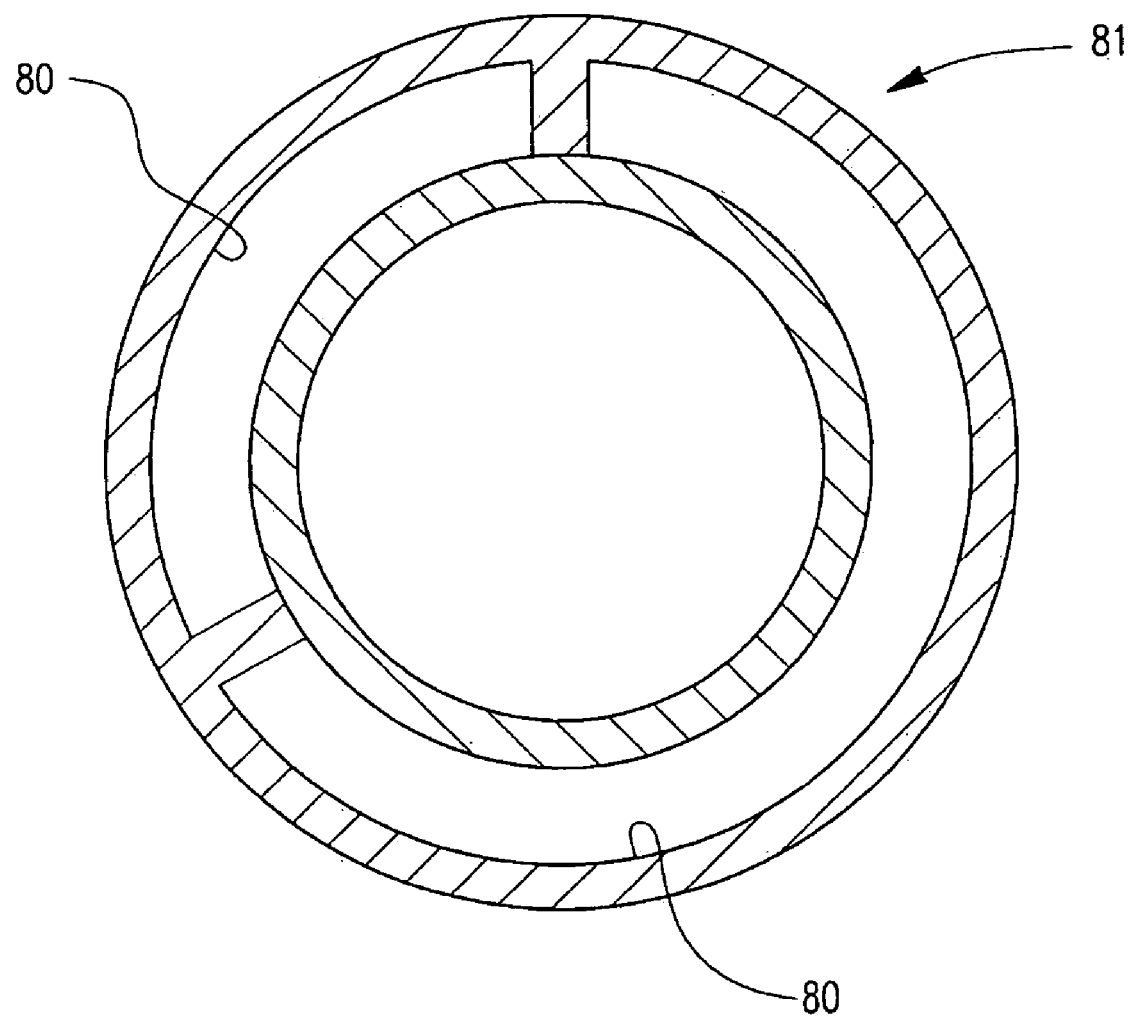

A second durable layer 44b is then provided over the first sacrificial structure 24 now filling the voids as shown in FIG. 6E. Both the mandrel 18 and the wires 74 may then be removed leaving a central lumen 78 and smaller lumens 76 which run in a longitudinal direction with the tube as shown in FIG. 6F. Solvent, indicated by arrow 77, may be flushed through lumens 76 to eliminate the sacrificial structure 24 and form channels 80 as shown in FIG. 6G. If a water dispersible or water soluble polymer is employed, water may be used to flush and eliminate sacrificial structure 24 from the structure. The resultant structure 81 shown in radial cross-section in FIG. 6G may also be further processed to form an expandable balloon member.

If the structure resulting from the process of FIGS. 6A-6G is a catheter shaft, the channels may be formed such that when the catheter assembly is in use, the channels are in fluid communication with a body lumen at the distal end region of the shaft.

Composite structures may also be prepared by the inventive processes. For example, materials employed for reinforcement of a medical device or component thereof may be employed herein. For example, both natural and synthetic fibers may be employed for wrapping, braiding, winding, roving, knitting, weaving, and so forth. Pre-formed fiber structures such as those in the form of a mesh, net, or chopped fiber mats may also be employed and slid into place over the desired structure. Furthermore, fibers which have been chopped into small pieces may be randomly applied. Monofilament as well as multi-filament fiber may be employed herein.

Both synthetic, i.e. man-made, and natural fibers may be employed herein. Natural fibers refer to those which occur in nature such as silk fibers produced by members of the phylum Arthropoda including arachnids and insects such as spiders, silk worms, black flies, wasps, and lacewing flies, while synthetic fibers refer to those fibers which are man-made such as those produced using recombinant protein technology. For example, synthetic spider silk may be produced using recombinant protein technology. Recombinant spider silk protein has been found to produce fiber having a suitable balance of properties including flexibility, strength and biocompatibility. Fibers of this nature are disclosed in commonly assigned copending U.S. patent application Ser. No. 10/862,250 filed Jun. 7, 2004, which is incorporated by reference herein in its entirety.

Examples of synthetic fibers include, but are not limited to, SPECTRA®, liquid crystal polymer fibers such as Ticona VECTRAN® liquid crystal polymer fibers, DuPont KEVLAR® aramid fiber, or other, polyimide, polyester, ultra high molecular weight polyethylene fibers, glass, flexible ceramic, carbon, metallic material, and so on and so forth. Nano fibers may also be employed herein.

The durable layer may be provided over the fibers by spraying, extruding, dipping, painting, and so forth. After removal of the mandrel and the sacrificial structure, another durable layer may be provided on the inner surface of the structure such as the member described in FIGS. 6A-6G. These members may be used as balloon preforms and further processed into balloon structures.

FIG. 7A-7D illustrate an embodiment whereby fiber reinforcement is inserted into an ablated area of the sacrificial structure, overcoated, and the sacrificial structure is eliminated. The inner surface of the resultant structure may be coated after elimination of the sacrificial structure such that the fiber reinforcement is encapsulated in the durable layer.

FIG. 7A illustrates a sacrificial structure 24 overcoated on mandrel 18. Voids 70 running in a longitudinal direction have been produced in sacrificial structure 24 can be produced using any method known in the art. Located in the voids 70 of sacrificial structure 24 are fibers 90. A composition for increasing friction or an adhesive composition may be employed between the fibers 90 and the sacrificial structure 24. The adhesive composition may be any suitable adhesive composition known in the art including thermoplastic and thermosetting compositions including radiation curable compositions such as those cured using UV radiation. Examples of suitable polymeric materials employed in the adhesive compositions include, but are not limited to polyurethanes, polyamides, polyolefins, polyesters, polyimides, polyethers, block copolymer elastomers including those having styrene end-blocks and midblocks of propylene, ethylene, butylenes, butadiene, isoprene, etc., as well as any copolymers thereof.

Gum rosins also find utility by themselves, or in combination with other adhesive components.

The sacrificial structure may then be coated with a durable layer 44. Mandrel 18 may then be removed and sacrificial structure 24 eliminated as described above. To fully encapsulate the fibers, another layer of durable material may be coated on the inside (not shown). The resultant member has projections 72 on the inner surface 73 of the member 12" defined by durable layer 44. Projections 72 project inward toward the lumen 75 of the member 12". The process results in a member 12" which may be employed as a balloon preform as shown in FIG. 7B. Fibers 90 are now embedded in the preform wall as shown by the cross-sectional depiction shown in FIG. 7C.

As shown in a radial cross-sectional view FIG. 7C, the fibers 90 are spaced equidistantly in a radial direction. In between the regions of the durable layer 44 having fibers 90, are regions which have no fibers. While, the member 12" of FIG. 7C, is shown having three regions comprising fibers, any number of fiber-containing regions may be incorporated into the structure as desired.

Figure 7D:
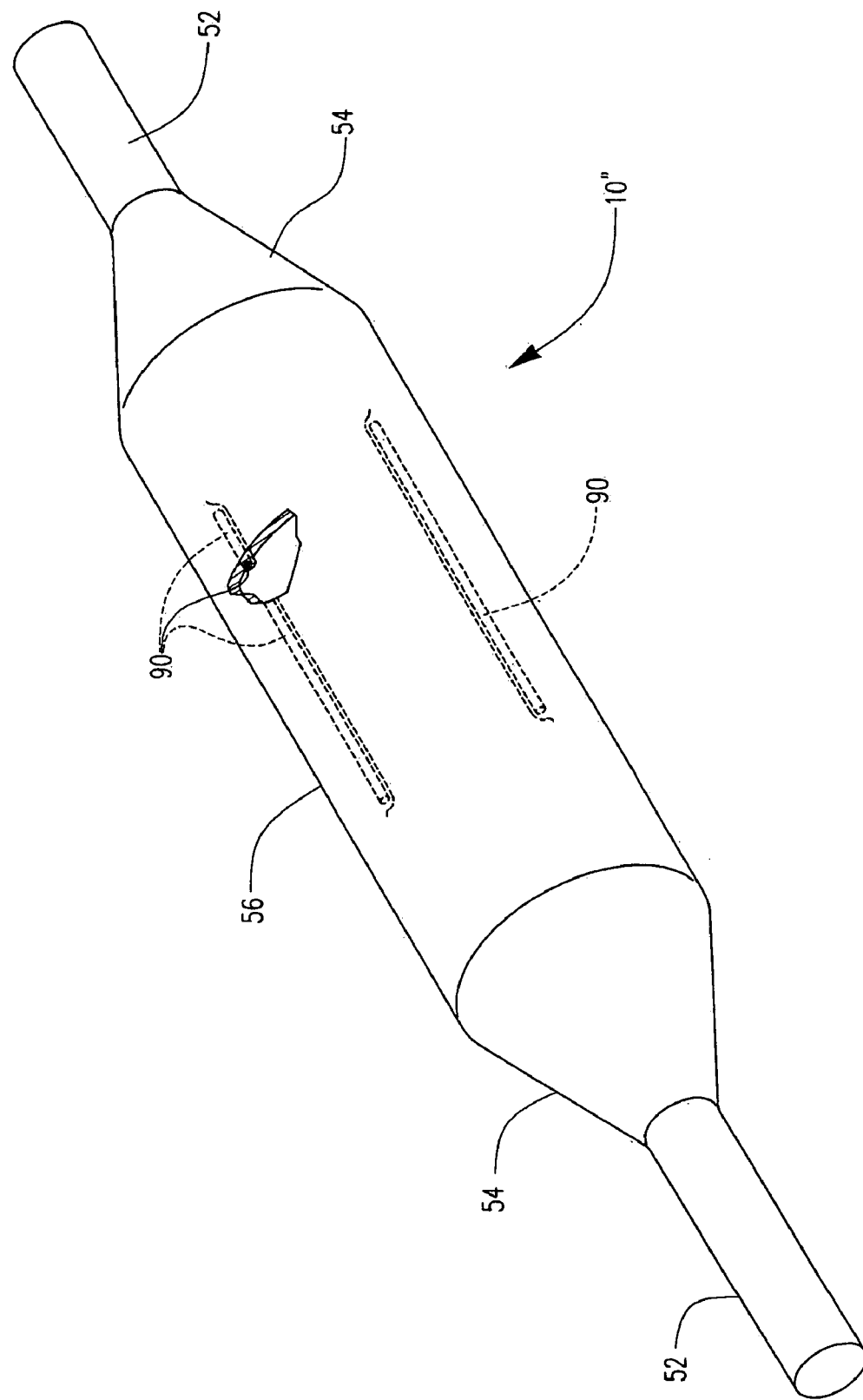

Member 12", employed as a balloon preform, may then be further processed as described above, using any balloon molding techniques known in the art as discussed above into expandable medical balloon 10" shown in FIG. 7D. In this embodiment, balloon body 56 is reinforced with fibers 90 which are located within projections 72 on the inner surface 73 of the balloon member, leaving the cone portions 54 and waist portions 52 unreinforced. The fibers 90 are shown extending longitudinally in balloon body 60.

Other types of materials may also be employed to build a composite structure such as radioapaque materials, conductive materials, ceramic, carbon, and so on and so forth. These types of materials can be readily embedded in the walls of the medical device employing the method of the present application.

Figure 8B:
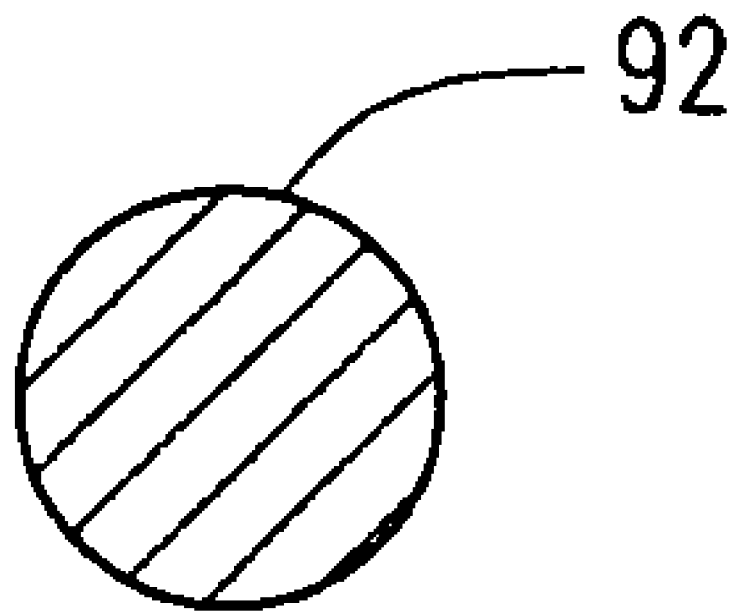
Figure 8C:
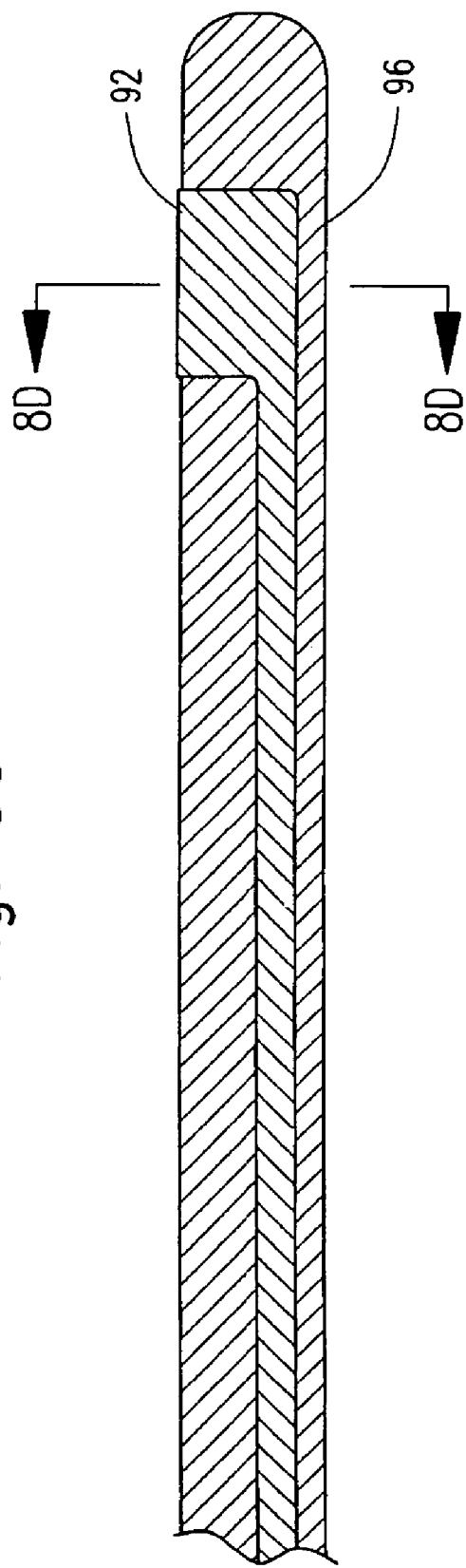
Figure 8D:
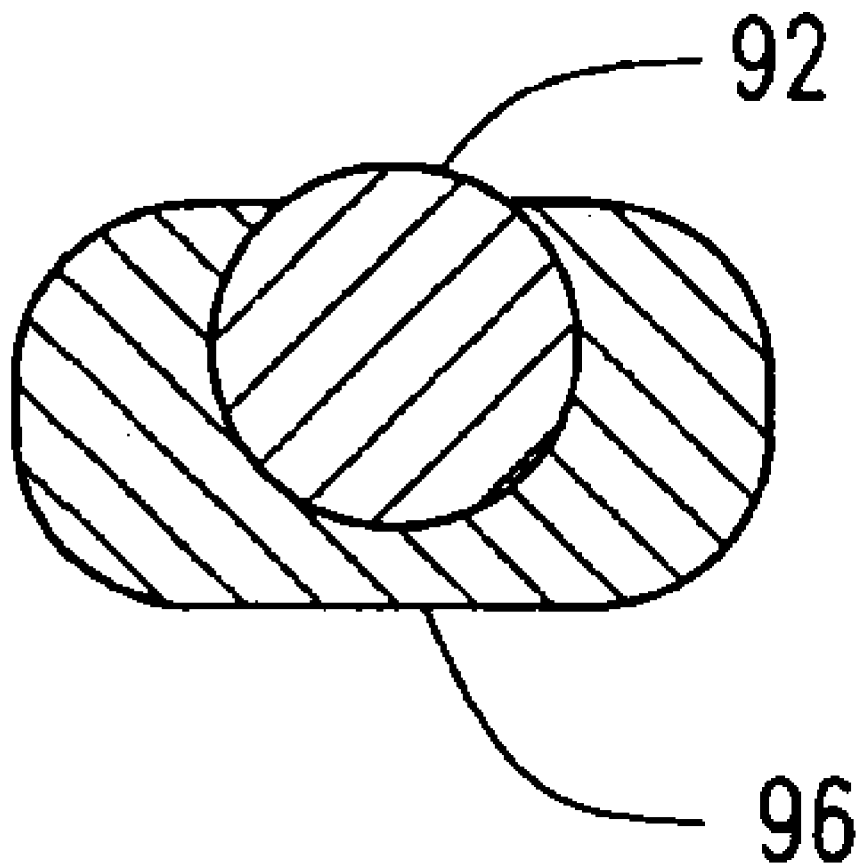

Another embodiment of the present invention illustrates formation of a distal sensor pocket for an intravascular ultrasound catheter assembly. A sacrificial structure 92 is formed according to the present specification as shown in partial longitudinal cross-section in FIG. 8A and in radial cross-section in FIG. 8B. Sacrificial structure 92 may be formed using any conventional molding techniques. A durable layer 96 may be applied to the sacrificial structure 92 using any conventional methods such as overcoating, molding, extruding, etc. as shown in FIG. 8C. FIG. 8D is a radial cross-sectional view taken at section 8D-8D in FIG. 8C.

Figure 8E:
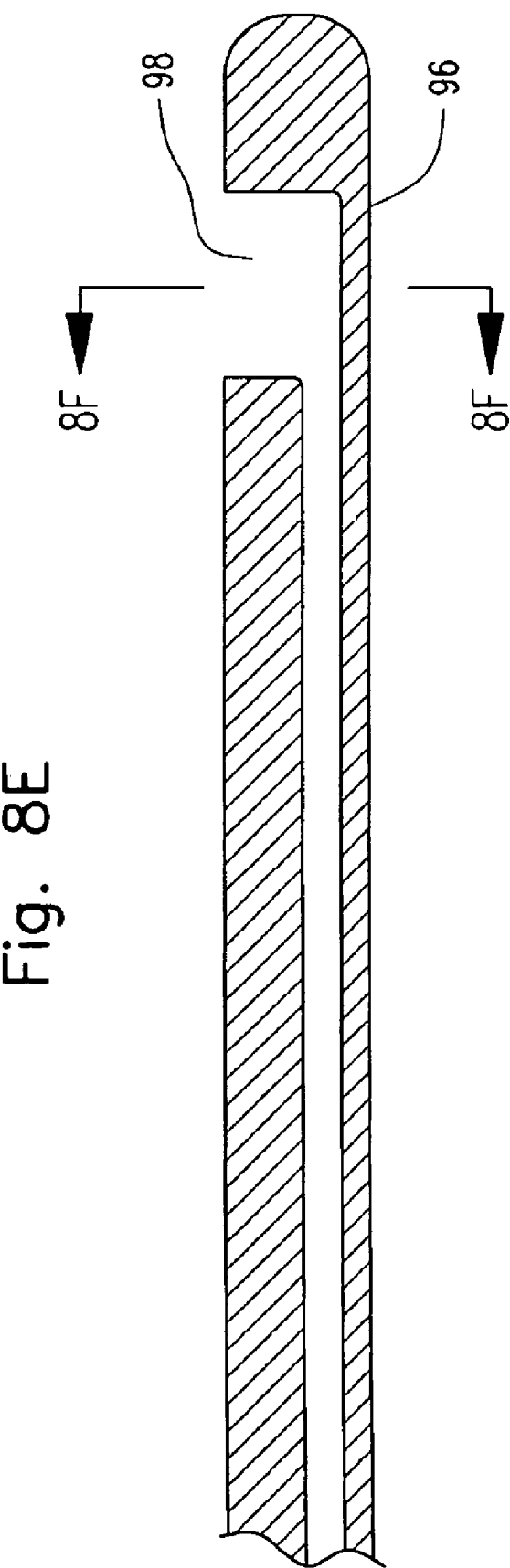
Figure 8F:
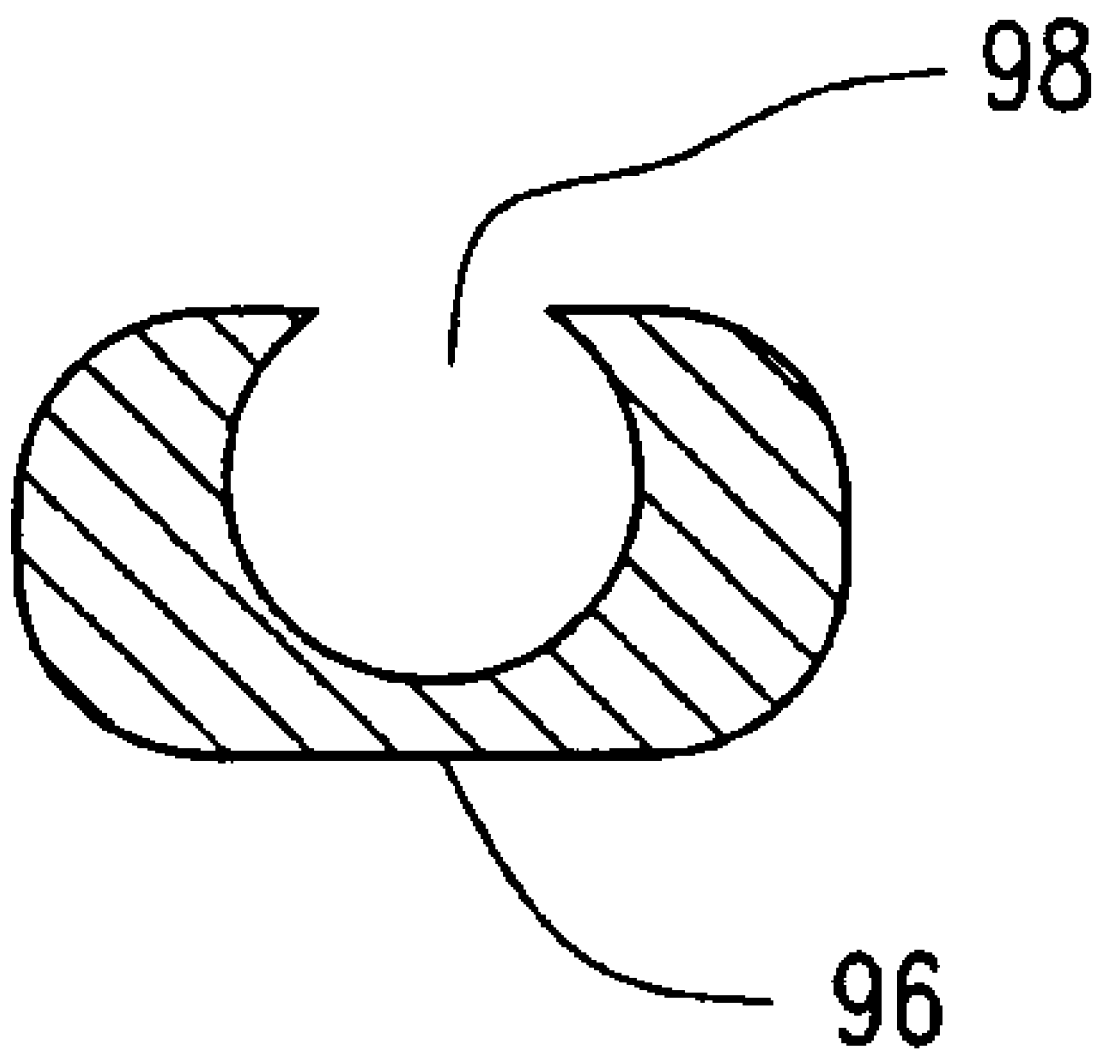

The sacrificial structure may then be eliminated using appropriate methods as determined by the type of material from which the sacrificial structure is formed. For example, water or solvent if the sacrificial structure is water dispersible or soluble. Once the sacrificial structure is eliminated, a sensor pocket 98 is formed at the distal end 94 of intravascular ultrasound catheter assembly 100 shown in partial longitudinal cross-section in FIG. 8E. FIG. 8F is a radial cross-sectional view taken at section 8F-8F in FIG. 8E.

Figure 9A:
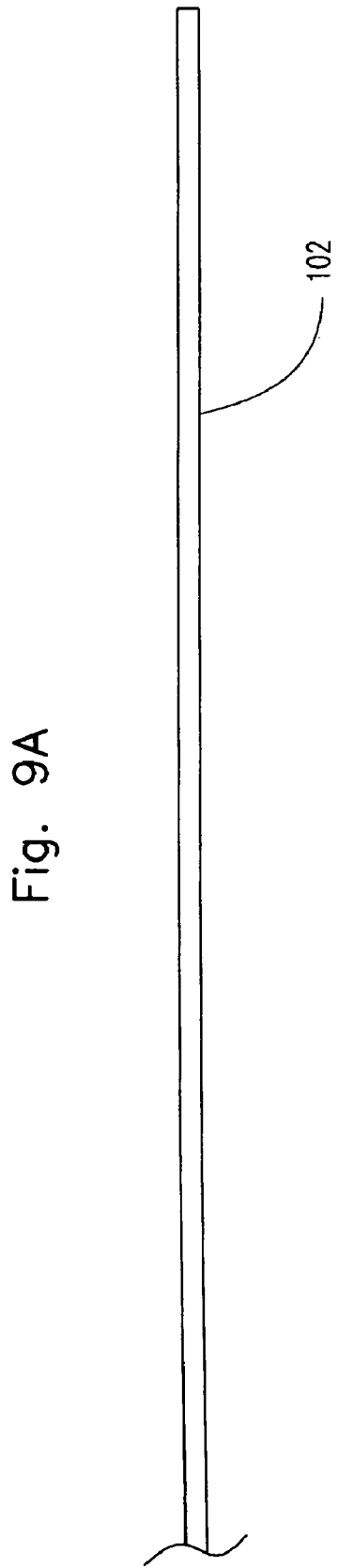
FIGS. 9A-9D illustrate an embodiment of the present invention whereby a distal guide wire tip having a hollow core is formed.
Figure 9B:
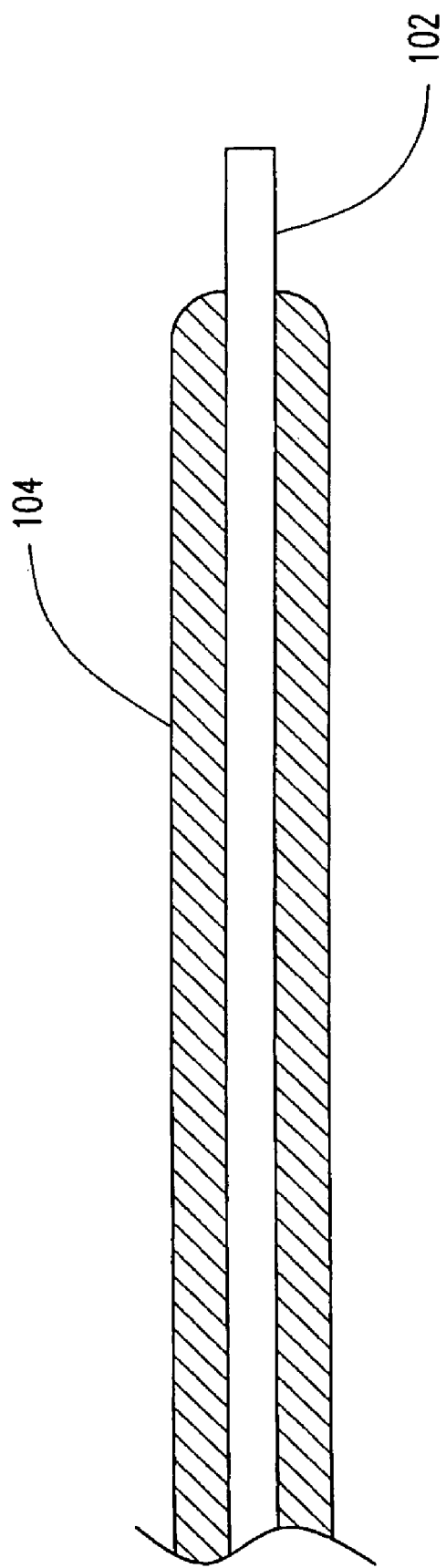
Figure 9C:
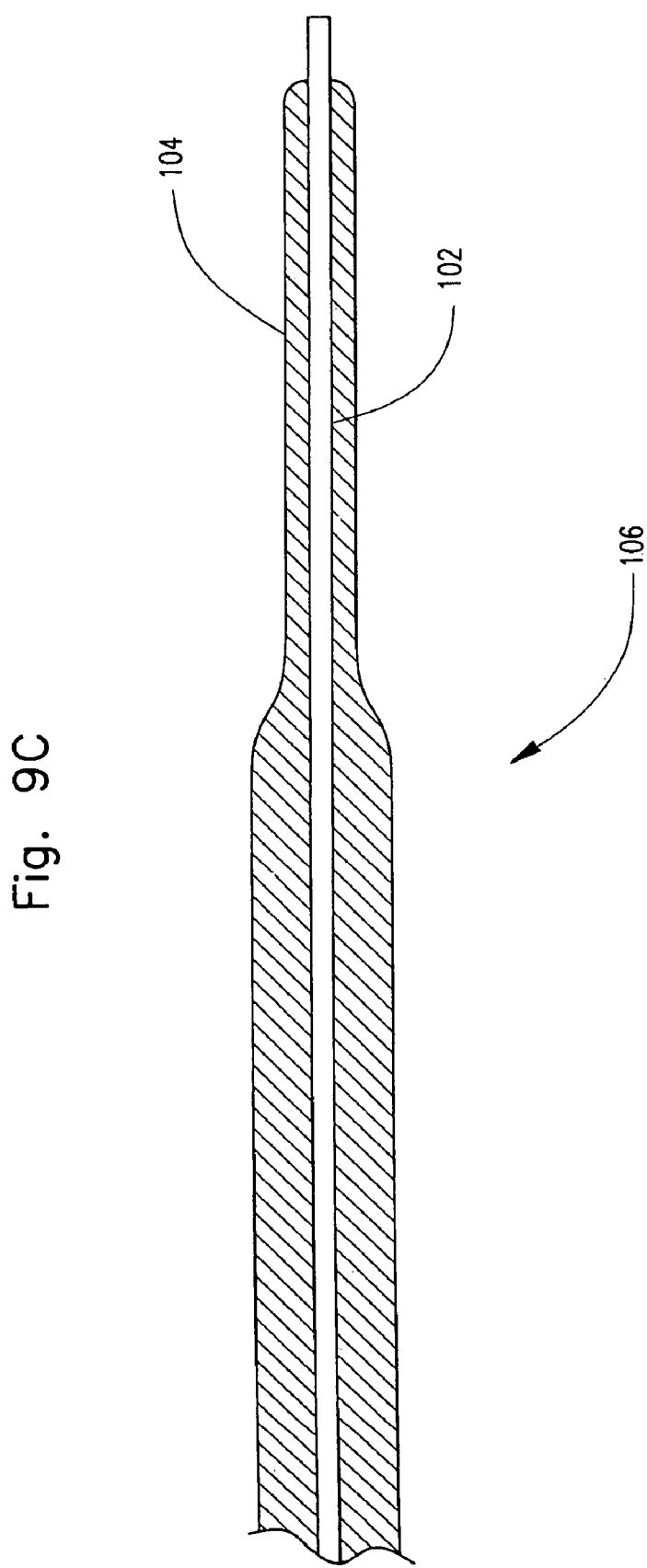
Figure 9D:
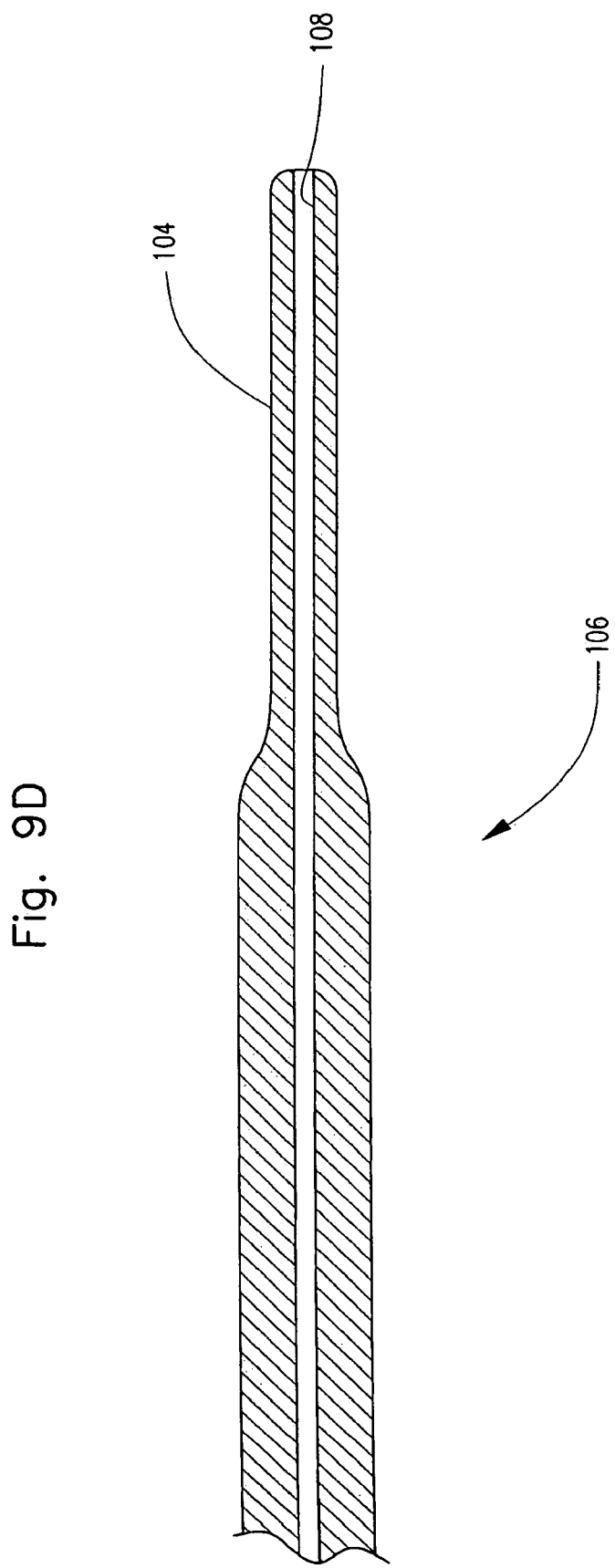

In another embodiment, a hollow polymeric guide wire tip is formed according to the invention. Sacrificial structure 102 is formed by molding or extruding, for example, and is shown in partial longitudinal cross-section in FIG. 9A. A durable layer 104 is deposited onto sacrificial structure by overcoating, extruding, coextruding, molding, etc. If extrusion techniques or overcoating techniques are employed, the durable layer may appear as shown in partial longitudinal cross-section in FIG. 9B. The durable layer 104 then may be manipulated using any known techniques such as by mechanical grinding or laser ablation techniques, to form a guide wire tip 106 having a configuration as shown in FIG. 9C or 9D. However, molding techniques may yield a guide wire tip 106 without any further manipulation, by employing a mold in the desired shape. The sacrificial structure 102, may then be eliminated, leaving a guide wire tip 106, having a hollow core 108. Guide wire tip 106 may then be secured to a hollow guide wire. The resultant assembly may be employed for delivery of therapeutic substances, for example.

The present invention may also be employed in the manufacture of ports for catheter assemblies. In one embodiment, the present invention is employed for making a guide wire port for a rapid exchange (RX) or single operator exchange (SOE) catheter delivery device.

Figure 10B:
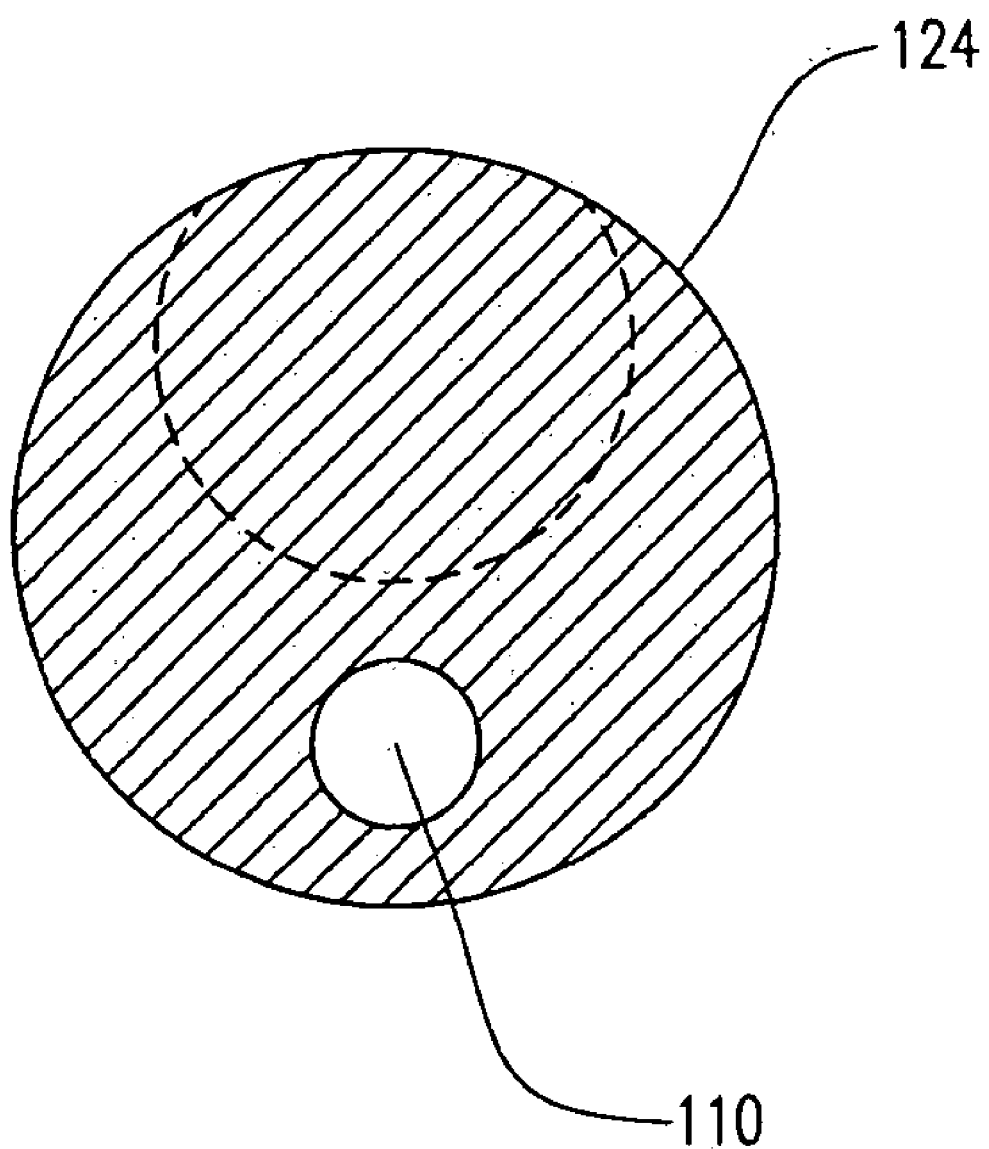
Figure 10C:
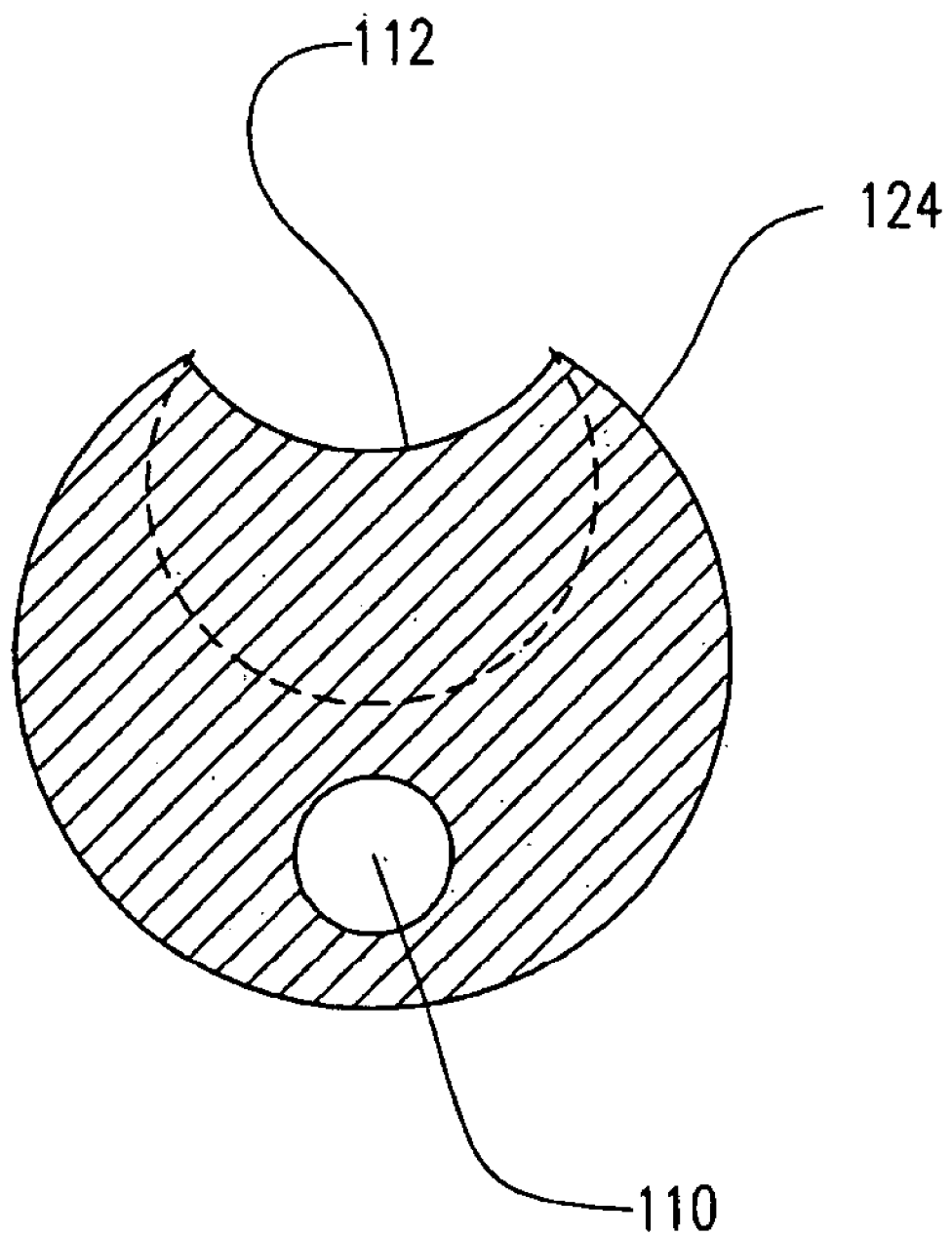
Figure 10D:
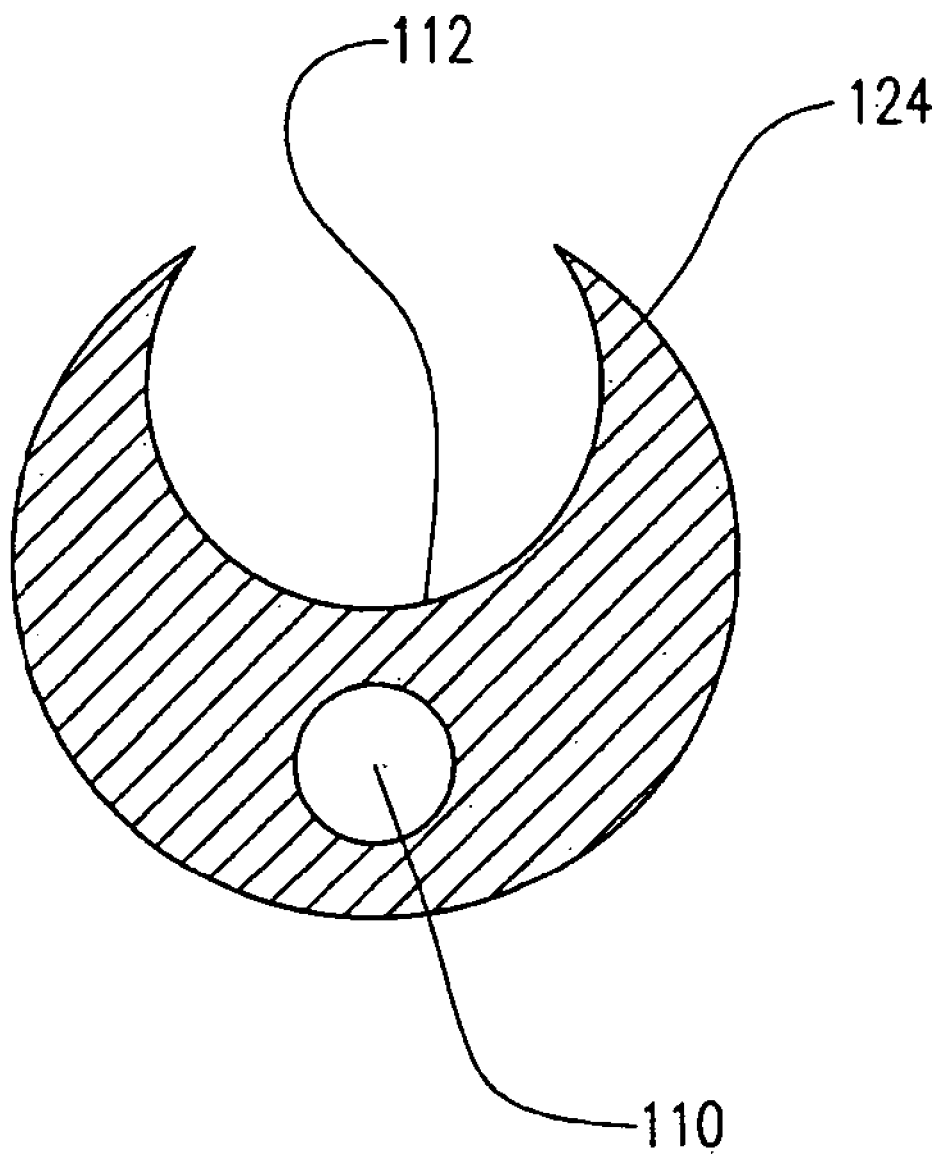

FIG. 10A is a perspective view of a sacrificial structure 124 having a lumen 110, and a moon-shaped depression 112 in the outer surface. Sacrificial structure 124 may be formed by injection molding and may be formed with materials described above such as PVA or PVOH which can be easily flushed from an assembly once the sacrificial structure 124 has served its purpose. FIGS. 10B, 10C and 10D are radial cross-sectional depictions taken at sections B-B, C-C and D-D of FIG. 10A respectively.

Sacrificial structure 124 may be inserted into an outer catheter shaft 114, having a side opening 116 formed in the wall 119 of catheter shaft 114 as shown perspectivley in FIG. 10E. Outer catheter shaft 114 may be formed using methods known in the art such as by extrusion, for example. This type of outer catheter shaft construction may be employed in a single operator exchange (SOE) catheter, which may also be referred to in the industry as a rapid exchange (RX) catheter.

Figure 10G:
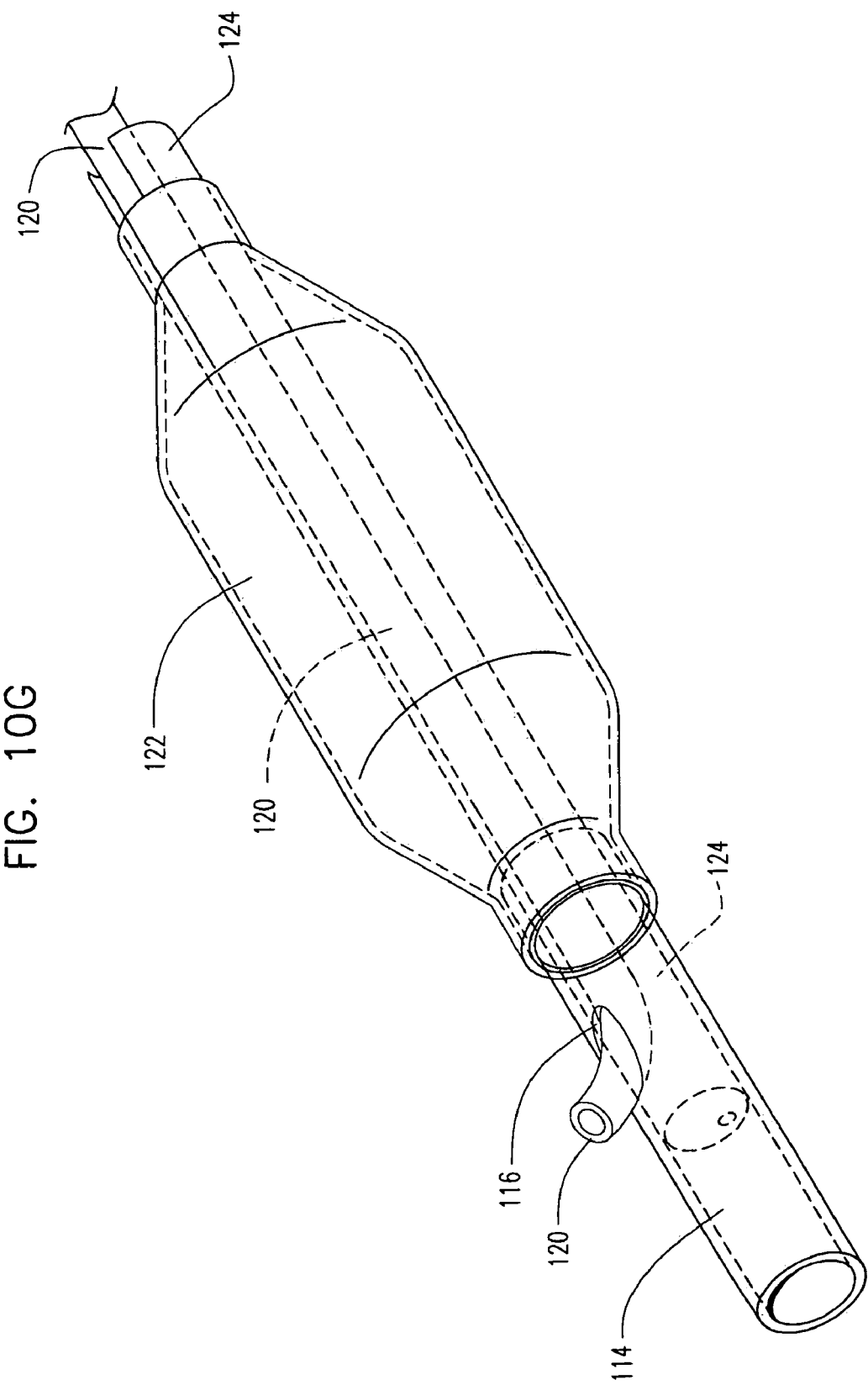

An inner catheter shaft 120 may then be inserted into the depression 112 of sacrificial structure 124 and through opening 116 in outer shaft 114 as depicted in FIGS. 10F and 10G. FIG. 10G is a fragmentary view of the distal end of the SOE catheter with catheter balloon 122. Inner shaft 120 may be secured to outer shaft 114 at opening 116 by methods known in the art including welding, adhesively, etc. Welding may be conducted using a laser, for example.

Balloon 122 may be secured to the distal end of the inner shaft 120 using methods known in the art by welding, adhesively, etc. as shown in FIG. 10G.

Once the balloon has been assembled over the outer shaft, the sacrificial structure may be removed by appropriate methods such as by flushing in the case of a sacrificial structure formed with PVA or PVOH.

FIG. 10H is a view similar to that of FIG. 10G with part removed by process, illustrating the balloon catheter assembly after the sacrificial structure has been removed from the assembly showing catheter balloon 122 over the inner shaft 120 at the distal end and over the outer shaft 114 at the proximal end of balloon 122. Removal of the sacrificial structure leaves a lumen between the inner shaft 120 and the outer shaft 114. At this time, inner shaft 120 may be secured at the distal end 126 of balloon 122 by methods known in the art including welding, adhesively, etc. FIG. 10I is a perspective view similar to that of FIG. 10H showing distal end of invention completely assembled with balloon 122 secured at the distal end to the inner shaft 120.

SOE catheters are discussed in U.S. Pat. No. 5,833,706 incorporated by reference herein in its entirety.

The above examples are intended for illustrative purposes only, and not as a limitation on the scope of the present invention.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A process of forming at least a portion of a medical device, the process comprising the steps of:
   providing a mandrel;
   providing a sacrificial structure on the mandrel, which at least in part defines the shape of said at least a portion of said medical device, the sacrificial structure comprises a member selected from the group consisting of ice, starch, sugar, waxes and solvatable polymeric materials;
   providing voids in the sacrificial structure;
   providing a durable layer over said sacrificial structure, the durable layer forming said at least a portion of said medical device, the durable layer fills the voids in the sacrificial structure; and
   eliminating said sacrificial structure after use, wherein upon elimination of the sacrificial structure patterns or voids are provided to a surface of the medical device.

2. The process of claim 1 wherein said sacrificial structure is provided on a preformed substrate layer of said at least a portion of said medical device.

3. The process of claim 1 wherein said sacrificial structure is provided by molding.

4. The process of claim 1 wherein said voids are provided in said sacrificial structure by grinding, cutting or laser ablating.

5. The process of claim 1 wherein a fiber material is provided in the voids.

6. The process of claim 1 wherein said durable layer comprises a polymeric composition and said durable layer fills said voids.

7. The process of claim 1 wherein said sacrificial structure defines the shape of said at least a portion of said medical device.

8. The process of claim 7 wherein a fiber web is provided over said sacrificial structure, the fiber web having an inner surface and an outer surface.

9. The process of claim 8 further comprising the step of providing a second durable layer on said inner surface of said fibers after eliminating said sacrificial structure.

10. The process of claim 1 wherein at least a portion of said medical device is a balloon preform.

11. The process of claim 10 further comprising the step of molding said balloon preform into a medical balloon.

12. The process of claim 1 wherein said mandrel comprises at least one member selected from the group consisting of ceramic, metal, polymeric compositions or a combination thereof.

13. The process of claim 1 wherein a first durable layer is provided on said mandrel and said durable layer is a second durable layer provided on said sacrificial structure.

14. The process of claim 13 further comprising the step of providing wire in said sacrificial structure and removing said wire after use.

15. The process of claim 1 wherein said sacrificial layer comprises a solvatable polymer is selected from the group consisting of polyvinyl alcohol, polyvinyl acetate or mixtures thereof.

16. The process of claim 15 further comprising the step of flushing said sacrificial structure with water at a temperature of about 25° C. to about 110° C.

17. The process of claim 1 wherein said durable layer comprises a thermoplastic composition, a thermosetting composition or mixtures thereof.

18. The process of claim 17 wherein said durable layer comprises a thermoplastic composition which comprises at least one polymer selected from the group consisting of polyesters, polyamides, polyolefins, polyurethanes, polyethers, polyimides, any copolymers thereof, styrenic block copolymers and mixtures thereof.

19. The process of claim 18 wherein said at least one polymer is selected from the group consisting of poly(ester block ester), poly(ester block ether), poly(ether block amide), polyalkylene terephthalate or mixture thereof.

20. A process of forming at least a portion of a medical device, the process comprising the steps of:
   providing a sacrificial structure, which at least in part defines the shape of said at least a portion of said medical device;
   providing a durable layer over said sacrificial structure, the durable layer forming said at least a portion of said medical device;
   providing voids in said sacrificial structure by grinding, cutting or laser ablating;
   providing a fiber material in the voids; and
   eliminating said sacrificial structure after use.

21. The process of claim 20 wherein said durable layer comprises a polymeric composition and said durable layer fills said voids.

22. A process of forming at least a portion of a medical device, the process comprising the steps of:
   providing a sacrificial structure which defines the shape of at least a portion of the medical device;
   providing a fiber web over the sacrificial structure, the fiber web having an inner and an outer surface;
   providing a durable layer over said sacrificial structure, the durable layer forming said at least a portion of said medical device; eliminating said sacrificial structure after use; and
   providing a second durable layer on said inner surface of said fibers after eliminating said sacrificial structure.

23. A process of forming at least a portion of a medical device, the process comprising the steps of:
   providing a mandrel;
   providing a first durable layer on said mandrel;
   providing a sacrificial structure on the first durable layer, the sacrificial structure defines the shape of at least a portion of the medical device;
   providing a plurality of wires in the sacrificial structure;
   providing voids or notches in the sacrificial structure
   providing a second durable layer over the sacrificial structure, the durable layer forming at least a portion of the medical device;
   eliminating the wire; and
   eliminating sacrificial structure after use.

* * * * *